US009364191B2

(12) United States Patent
Ning et al.

(10) Patent No.: US 9,364,191 B2
(45) Date of Patent: Jun. 14, 2016

(54) METHOD AND APPARATUS OF SPECTRAL DIFFERENTIAL PHASE-CONTRAST CONE-BEAM CT AND HYBRID CONE-BEAM CT

(71) Applicant: University of Rochester, Rochester, NY (US)

(72) Inventors: Ruola Ning, Fairport, NY (US); Weixing Cai, Rochester, NY (US)

(73) Assignee: UNIVERSITY OF ROCHESTER, Rochester, NY (US)

( * ) Notice: Subject to any disclaimer, the term of this patent is extended or adjusted under 35 U.S.C. 154(b) by 361 days.

(21) Appl. No.: 13/843,508

(22) Filed: Mar. 15, 2013

(65) Prior Publication Data
US 2014/0226783 A1    Aug. 14, 2014

Related U.S. Application Data

(60) Provisional application No. 61/763,159, filed on Feb. 11, 2013.

(51) Int. Cl.
*A61B 6/03*    (2006.01)
*G01N 23/087*    (2006.01)
*G06T 11/00*    (2006.01)
*A61B 6/00*    (2006.01)
*G01N 23/20*    (2006.01)

(52) U.S. Cl.
CPC ............ *A61B 6/5235* (2013.01); *A61B 6/4241* (2013.01); *A61B 6/482* (2013.01); *G01N 23/087* (2013.01); *G01N 23/20091* (2013.01); *A61B 6/032* (2013.01); *A61B 6/4035* (2013.01); *A61B 6/4085* (2013.01); *A61B 6/4291* (2013.01); *A61B 6/484* (2013.01); *A61B 6/502* (2013.01); *G06T 11/005* (2013.01); *G06T 2207/10081* (2013.01); *G06T 2207/20212* (2013.01)

(58) Field of Classification Search
CPC ............ A61B 6/00; A61B 6/03; A61B 6/032; A61B 6/035; A61B 6/40; A61B 6/4064; A61B 6/4085; A61B 6/42; A61B 6/4208; A61B 6/4233; A61B 6/4241; A61B 6/421; A61B 6/44; A61B 6/4447; A61B 6/48; A61B 6/482; A61B 6/484; A61B 6/488; A61B 6/50; A61B 6/502; A61B 6/52; A61B 6/5205; A61B 6/5211; A61B 6/5229; A61B 6/5235; G01T 1/00; G01T 1/16; G01T 1/1606; G01T 1/161; G01T 1/17; G01T 1/20; G01T 1/2018; G01T 1/24; G01T 1/36; G01T 1/362; G01T 1/366; G01N 23/00; G01N 23/02; G01N 23/04; G01N 23/046; G01N 23/06; G01N 23/08; G01N 23/083; G01N 23/087; G01N 23/20075; G01N 23/20091; G06T 1/00; G06T 1/0007; G06T 11/00; G06T 11/003; G06T 11/005; G06T 2200/00; G06T 2200/04; G06T 2201/00; G06T 2207/00; G06T 2207/10072; G06T 2207/10081; G06T 2007/20212; G06T 2207/20212; G06T 2207/20216; G06T 2207/30; G06T 2207/30004; G06T 2207/30068; G06T 2207/22; G21K 2207/00; G21K 2207/005; G02B 5/18; G02B 5/1814; G02B 5/1819; G02B 5/1823; G02B 5/1842; G02B 5/1866; G02B 5/1871; G02B 5/21; G02B 26/00; G02B 26/06; G02B 27/00; G02B 27/44; G02B 27/50; G02B 27/52; G02B 27/60; H01L 27/144; H01L 27/146; H01L 27/14601; H01L 27/14643; H01L 27/14658; H01L 27/14676; H01L 27/148; H01L 27/307; H01L 27/308
USPC ............ 378/4–20, 37, 51, 62, 98, 98.2, 98.8, 378/98.9, 98.12, 204, 210, 901; 257/414, 257/428, 429, E27.14, E27.146
See application file for complete search history.

(56) References Cited

U.S. PATENT DOCUMENTS

| | | |
|---|---|---|
| 3,165,630 A | 1/1965 | Bielat et al. |
| 3,963,933 A | 6/1976 | Henkes, Jr. |
| 3,973,126 A | 8/1976 | Redington et al. |
| 4,015,836 A | 4/1977 | Redington et al. |
| 4,255,014 A | 3/1981 | Ellis |
| 4,423,047 A | 12/1983 | Benneche et al. |
| 4,549,307 A | 10/1985 | Macovski |
| 4,891,829 A | 1/1990 | Deckman et al. |
| 5,023,894 A | 6/1991 | Yamashita et al. |
| 5,073,910 A | 12/1991 | Eberhard et al. |
| 5,133,020 A | 7/1992 | Giger et al. |
| 5,170,439 A | 12/1992 | Zeng et al. |
| 5,182,624 A | 1/1993 | Tran et al. |
| 5,262,649 A | 11/1993 | Antonuk et al. |
| 5,375,156 A | 12/1994 | Kuo-Petravic et al. |
| 5,390,112 A | 2/1995 | Tam |
| 5,396,072 A | 3/1995 | Schiebel et al. |
| 5,400,255 A | 3/1995 | Hu |
| 5,448,607 A | 9/1995 | McKenna |
| 5,459,769 A | 10/1995 | Brown |
| 5,526,394 A | 6/1996 | Siczek et al. |
| 5,564,438 A | 10/1996 | Merchant |
| 5,598,453 A | 1/1997 | Baba et al. |
| 5,602,891 A | 2/1997 | Pearlman |
| 5,609,152 A | 3/1997 | Pellegrino et al. |
| 5,663,995 A | 9/1997 | Hu |
| 5,784,481 A | 7/1998 | Hu |
| 5,802,133 A | 9/1998 | Kawai et al. |
| 5,802,137 A | 9/1998 | Wilkins et al. |
| 5,812,629 A | 9/1998 | Clauser |
| 5,864,146 A | 1/1999 | Karellas |
| 5,865,146 A | 2/1999 | Markham |
| 5,907,594 A | 5/1999 | Lai |
| 5,909,476 A | 6/1999 | Cheng et al. |
| 5,949,811 A | 9/1999 | Baba et al. |
| 5,949,850 A | 9/1999 | Tang |
| 5,959,811 A | 9/1999 | Richardson |
| 5,999,587 A | 12/1999 | Ning et al. |
| 6,002,738 A | 12/1999 | Cabral et al. |
| 6,014,419 A | 1/2000 | Hu |
| 6,018,564 A | 1/2000 | Wilkins et al. |
| 6,038,282 A | 3/2000 | Wiesent et al. |
| 6,047,042 A | 4/2000 | Khutoryansky et al. |
| 6,049,343 A | 4/2000 | Abe et al. |
| 6,075,836 A | 6/2000 | Ning |
| 6,125,193 A | 9/2000 | Han |
| 6,226,353 B1 | 5/2001 | Wilkins et al. |
| 6,262,818 B1 | 7/2001 | Cuche et al. |
| 6,282,256 B1 | 8/2001 | Grass et al. |
| 6,298,110 B1 | 10/2001 | Ning |
| 6,298,114 B1 | 10/2001 | Yoda |
| 6,477,221 B1 | 11/2002 | Ning |
| 6,480,565 B1 | 11/2002 | Ning |
| 6,504,892 B1 | 1/2003 | Ning |
| 6,618,466 B1 | 9/2003 | Ning |
| 6,987,831 B2 | 1/2006 | Ning |
| 7,023,951 B2 | 4/2006 | Man |
| 7,103,135 B2 | 9/2006 | Koppe et al. |
| 7,245,755 B1 | 7/2007 | Pan et al. |
| 7,636,461 B2 | 12/2009 | Spies et al. |
| 7,697,660 B2 | 4/2010 | Ning |
| 2003/0073893 A1 | 4/2003 | Hsieh |
| 2004/0017881 A1 | 1/2004 | Cesmeli et al. |
| 2004/0066876 A1 | 4/2004 | Tam |
| 2004/0081273 A1 | 4/2004 | Ning |
| 2004/0252809 A1 | 12/2004 | Kotian et al. |
| 2005/0117699 A1 | 6/2005 | Yoneyama |
| 2005/0141669 A1 | 6/2005 | Shimono et al. |
| 2005/0286680 A1 | 12/2005 | Momose |
| 2006/0039532 A1 | 2/2006 | Wu et al. |
| 2006/0039536 A1 | 2/2006 | Nishide et al. |
| 2006/0094950 A1 | 5/2006 | Ning |
| 2006/0120508 A1 | 6/2006 | Chen et al. |
| 2007/0053477 A1 | 3/2007 | Ning |
| 2007/0183559 A1 | 8/2007 | Hempel |
| 2007/0253528 A1 | 11/2007 | Ning et al. |
| 2008/0226017 A1* | 9/2008 | Altman ................ G06T 7/0004 378/4 |
| 2009/0092227 A1 | 4/2009 | David et al. |
| 2010/0220832 A1* | 9/2010 | Ning ................ A61B 6/032 378/4 |
| 2011/0142316 A1* | 6/2011 | Wang ................ G06T 11/006 382/131 |
| 2013/0028379 A1* | 1/2013 | Nelson ................ G01N 23/04 378/62 |

FOREIGN PATENT DOCUMENTS

| | | |
|---|---|---|
| CN | 1965760 A | 5/2007 |
| CN | 101044987 A | 10/2007 |
| CN | 101622526 A | 1/2010 |
| DE | 2633828 A1 | 2/1977 |
| DE | 2636761 A1 | 3/1977 |
| DE | 2716818 A1 | 11/1977 |
| DE | 4116381 C1 | 7/1992 |
| DE | 4423047 A1 | 1/1996 |
| DE | 4434948 A1 | 4/1996 |
| DE | 19502574 A1 | 8/1996 |
| DE | 69129032 T2 | 8/1998 |
| DE | 19721535 A1 | 11/1998 |
| DE | 69321221 T2 | 2/1999 |
| DE | 19835451 A1 | 3/1999 |
| DE | 69413212 T2 | 3/1999 |
| DE | 19840405 A1 | 4/1999 |
| DE | 19800946 A1 | 7/1999 |
| DE | 19914296 A1 | 10/1999 |
| EP | 0105618 A2 | 4/1984 |
| EP | 0492895 A2 | 7/1992 |
| EP | 0592093 A2 | 4/1994 |
| EP | 0 948 930 A1 | 10/1999 |
| EP | 1004275 A1 | 5/2000 |
| EP | 1 149 559 A1 | 10/2001 |
| EP | 1231860 A1 | 8/2002 |
| FR | 2648589 A1 | 12/1990 |
| JP | 7303633 A | 11/1995 |
| JP | 2000023956 A | 1/2000 |
| WO | 93/17620 A1 | 9/1993 |
| WO | 9515072 A1 | 6/1995 |
| WO | 9615072 A1 | 5/1996 |
| WO | 9634416 A1 | 10/1996 |
| WO | 9635372 A2 | 11/1996 |
| WO | 9712550 A1 | 4/1997 |
| WO | 9742877 A1 | 11/1997 |
| WO | 9858389 A1 | 12/1998 |
| WO | 99/01066 A1 | 1/1999 |
| WO | 0135829 A1 | 5/2001 |
| WO | 2004/043535 A2 | 5/2004 |
| WO | 2006003578 A1 | 1/2006 |
| WO | 2007100823 A2 | 9/2007 |

OTHER PUBLICATIONS

Siewerdsen, et al., "Cone-beam computed tomography with a flat-panel imager: Effects of image lag", Medical Physics, 1999, vol. 26, p. 2635-2647.

Siewerdswen, et al., "Optimization of x-ray imaging geometry (with specific application to flat-panel cone-beam computed tomography)", Medical Physics, 2000, vol. 27, p. 1903-1914.

Arfelli, F., "Synchrontron light and imaging systems for medical radiology", Nuclear Instruments & Methods in Physics Research, Section—A: Accelerators, Sepctrometers, Detectors and Associated Equipment, 20001101 Elsevier, Amsterdam, NL, vol. 454, p. 11-25.

Ning, et al., "Flat panel dectector-based cone-beam volume CT angiography imaging: system evaluation", IEEE Transactions on Medcial Imaging, vol. 19 Issue 9, p. 949-963 (Abstract) (Sep. 2000).

Waters, et al., "High energy X-ray Radiography and Computed Tomography of Bridge Pins", Second Japan-US Symposium of Advances in Nondestructive Testing, Oahu, Hawaii, 1999.

Hsieh, J., "Computed Tomography, Principles, Design, Artifats, and Recent Advances", (11 pages).

Faris et al., "Three-dimensional beam-deflection optical tomography of a supersonic jet", Applied Optics, 1988, pp. 5202-5212, vol. 27, Issue 24.

Wu, et al., "X-Ray Cone-Beam Phase Tomography Formulas Based on Phase-Attenuation Duality", Optics Express, Aug. 2005, pp. 6000-6014, vol. 13, No. 16.

Momose, "Demonstration of Phase-Contrast X-Ray Computed Tomography Using an X-Ray Interferometer", Nuclear Instruments and Methods in Physics Research Section A, Mar. 1994, pp. 622-628, vol. 352, No. 3.

Mayo, et al., "X-Ray Phase-Contrast Microscopy and Microtomography", Optics Express Sep. 2003, pp. 2289-2302, vol. 11, No. 19.

Chapman, et al., "Diffraction Enhanced X-Ray Imaging," Physics in Medicine and Biology, Aug. 1997, pp. 2015-2025, vol. 42, No. 11.

Nath, et al., "Wavelet based compression and denoising of optical tomography", Aug. 15, 1999, pp. 37-46, vol. 167, Issues 1-6.

Boone et al.,"Dedicated Breast CT: Radiation Dose and Image Quality Evaluation", Radiology, Dec. 2001, pp. 657-667, vol. 221, No. 3.

Chen et al., "Cone-beam volume CT breast imaging: Feasibility Study", Medical Physics, May 2002, pp. 755-770, vol. 29, Issue 5, AIP, Melville, NY, US.

Anderson et al., "An Interactive Computer Graphics System for the Computed Tomographic Breast Scanner (CT/M)", 1979, pp. 350-354.

Chang et al., "Computed Tomography of the Breast", Radiology, 1977, pp. 827-829, vol. 124, No. 3.

Chang et al., "Computed Tomographic Evaluation of the Breast", American Journal of Roentgenology, pp. 459-484, vol. 131.

Chang et al., "Computed Tomography in Detection and Diagnosis of Breast Cancer," Cancer, August Supplement, 1980, pp. 939-946, vol. 46.

Hu, "A New Cone Beam Reconstruction Algorithm for the Circular Orbit," IEEE Nuclear Science Symposium and Medical Imaging Conference 1994 conference Record, 1995, pp. 1261-1265, vol. 3.

Hu, "Exact Regional Reconstruction of Longitudinally-Unbounded Objects using the Circle-and Line Cone Beam Tomographic System," SPIE, 1997, pp. 441-444, vol. 3032.

Kak et al., "Principles of Computerized Tomographic Imaging", Classics in Applied Mathematics, 1988, pp. 99-107, Siam.

Kornmesser et al., "Fast Feldkamp—reconstruction for Real-time Reconstruction Using C-arm Systems," Proceedings of the 16th International Congress and Exposition on Computer Assisted Radiology and Surgery (CARS 2002), 2002, pp. 430-434 ISBN 3-540-43655-3.

Tang et al., "A Three-dimensional Weighted Cone Beam Filtered Back Projection (CB-FBP) Algorithm for Image Reconstruction in a Volumetric CT Under a Circular Source Trajectory", Physics in Medicine and Biology, Aug. 3, 2005, pp. 3889-3906, vol. 50.

Yang, et al., "Modified FDK half-scan (MFDKHS) Scheme on Flat Panel Detector-Based Cone-Beam CT," Apr. 2005, SPIE vol. 5745, Proceedings of Medical Imaging 2005: Physics in Imaging held Feb. 13, 2005, pp. 1030-1037.

Yang, et al., "Implementation & Evaluation of the Half-Scan Scheme Based on CBCT (Cone-Beam CT) System", 2004, SPIE vol. 5368, Proceedings of Medical Imaging 2004: Physics, pp. 542-551.

Yu et al., "Application of Asymmetric Cone-beam CT in Radiotherapy", 2004, IEEE Nuclear Science Symposium Conference Record 2004, pp. 3249-3252, vol. 5.

Zhao et al., "Feldkamp-Type Cone-Beam Tomography in the Wavelet Framework", IEEE Transactions on Medical Imaging, Sep. 2000, pp. 922-929, vol. 19, Issue 9.

Weitkamp et al., "X-ray phase imaging with a grating interferometer," Optics Express, 2005, pp. 6296-6304, vol. 13, Issue 16.

Pierre Grangeat; "Mathematical Framework of Cone Beam 3D REconstruction Via the First Derivative of the RAdon Transform"; 85 X-38041 Grenoble Cedex—France.

Weng, Zeng and Gullbuerg; "A Reconstruction Algorithm for Helical Cone-Beam Spect"; Medical Imaging Research Laboratory, Dept. of Radiology, University of Utah, Salt Lake City, UT 84132, 0018-9499/93503.00 (1993) IEEE.

Feldkamp, Davis, and Kress; "Pracical Cone-Beam Algorithm", Research Staff, Ford Motor Company, Dearborn, Michigan; 0740-3232/84/060612-08$02.00 (1984) J. Opt. Soc. Am. A/vol. 1, No. 6/Jun. 1984.

Smith, "Image Reconstruction from Cone-Beam Projections: Necessary and Sufficient Conditions and Reconstruction Methods", IEEE Transactions on Medical Imaging, vol. M1-4, No. 1, Mar. 1985.

Tuy; "An Inversion Formula for Cone-Beam Reconstruction"; SIAM J. Appl. Math. vol. 43, No. 3, Jun. 1983.

Jaffray; Siewerdsen; and Drake; "Performance of a Volumetric CT Scanner Based Upon a Flat-Panel Imager"; William Beaumont Hospital, Royal Oak, MI 48073; SPIE vol. 3659; Feb. 1999.

Ivanovic; Weber; Loncaric; "Multi-Pinhole Collimator Optimization for High Resolution SPECT Imaging" University of California Davis Medical Center, Sacramento, CA 95817; 0-7803-4258-5/98 (1998 IEEE).

Boone J. M. et al., "Dedicated Breast CT: Radiation Dose and Image Quality Evaluation", Radiology—Dec. 2001, vol. 221, No. 3, Dec. 2001 pp. 657-667, XP002558707.

Antonuk, et al., "Thin-Film, Flat-Panel, Composite Imagers for Projection and Tomographic Imaging," IEEE Transactions on Medical Imaging, Sep. 1994, pp. 482-490, vol. 13, No. 2.

Horsman, et al., "Isotope Computed Tomography Using Cone-Beam Geometry: A Comparison of Two Reconstruction Algorithms," Physics in Medicine and Biology, Oct. 1987, pp. 1221-1235, vol. 32, No. 10.

Ning, et al., "Image Intensifier-Based Computer Tomography Volume Scanner for Angiography," Academic Radiology, Apr. 1996, pp. 344-350, vol. 3, No. 4.

Thomlinson, et al., "Diffraction Enhanced X-Ray Imaging," Physics in Medicine and Biology, Aug. 1997, pp. 2015-2025, vol. 42, No. 11.

Anastasio, et al., "Analytic Image Reconstruction in Local Phase-Contrast Tomography," Phys Med Biol, 2004, pp. 121-144, vol. 49.

Bronnikov, "Theory of Quantitative Phase-Contrast Computed Tomography," J Opt Soc Am. A, Mar. 2002, pp. 472-480, vol. 19, No. 3.

Hwu, et al., "Coherence Based Contrast Enhancement in X-Ray Radiography with a Photoelectron Microscope," Applied Physics Letters, Oct. 1999, pp. 2377-2379, vol. 75, No. 16.

Mayo, et al., "Quantitative X-Ray Projection Microscopy: Phase-Contrast and Multi-Spectral Imaging," Journal of Microscopy, Aug. 2002, pp. 79-96, vol. 207, pt 2.

Momose, "Phase-Sensitive Imaging and Phase Tomography Using X-Ray Interferometers," Optics Express, Sep. 2003, pp. 2303-2314, vol. 11, No. 19.

Pogany, et al., "Contrast and Resolution in Imaging with Microfocus X-Ray Source," Rev. Sci. Instrum., Jul. 1997, pp. 2774-2782, vol. 68, No. 7.

Stampanoni, et al., "Phase Contrast Imaging: A New Tool for Biomedical Investigations," IEEE, 2006, pp. 1100-1103.

Tafforeau, et al., "Applications of X-Ray Synchrotron Microtomography for Non-Destructive 3D Studies of Paleontological Specimens," Appl Phys A, 2006, pp. 195-202, vol. 83.

Van Geet, et al., "Towards 3-D Petrography: Application of Microfocus Computer Tomography in Geological Science," Computers and.

Wu, et al., "A General Theoretical Formalism for X-Ray Phase Contrast Imaging," Journal of X-Ray Science and Technology, 2003, pp. 33-42.

Wu, et al., "An Experimental Method of Determining Relative Phase-Contrast Factor for X-Ray Imaging Systems," Med Phys, May 2004, pp. 997-1002, vol. 31, No. 5.

Wu, et al., "Clinical Implemenation of X-Ray Phase-Contrast Imaging: Theoretical Foundations and Design Considerations," Med Phys, Aug. 2003, pp. 2169-2179, vol. 30, No. 8.

Jaffray, et al., "Cone-beam computed tomography with a flat-panel imager: Initial performance characterization", Med. Phys. 27(6), Jun. 2000, p. 1311-1323.

Love, et al., "Scatter estimation for a digital radiographic system using convolution filtering", Med. Phys. 14, 178 (1987).

Tang, et al., "2D wavelet-analysis-based calibration technique for flat panel imaging dectectors: Application in cone beam volume CT", Proceedings of SPIE—The Internat'l Society for Optical Engineering 1999 Society of Photo-Optical Instrumentation Engineers, vol. 3659, p. 806-816.

(56) References Cited

OTHER PUBLICATIONS

Siewerdsen, et al., "A ghost story: Spatio-temporal response characteristics of an indirect-detection flat-panel imager", Medical Physics, 1999, vol. 26, p. 1624-1641.

\* cited by examiner

*Primary Examiner* — Anastasia Midkiff
(74) *Attorney, Agent, or Firm* — Cooper & Dunham LLP

(57) ABSTRACT

DPC (differential phase contrast) images are acquired for each photon energy channel, which are called spectral DPC images. The final DPC image can be computed by summing up these spectral DPC images or just computed using certain 'color' representation algorithms to enhance desired features. In addition, with quasi-monochromatic x-ray source, the required radiation dose is substantially reduced, while the image quality of DPC images remains acceptable.

44 Claims, 31 Drawing Sheets

(a)

(b)

Prior Art

Prior Art

Prior Art

Prior Art

METHOD AND APPARATUS OF SPECTRAL DIFFERENTIAL PHASE-CONTRAST CONE-BEAM CT AND HYBRID CONE-BEAM CT

REFERENCE TO RELATED APPLICATION

The present application claims the benefit of U.S. Provisional Patent Application No. 61/763,159, filed Feb. 11, 2013, whose disclosure is hereby incorporated by reference in its entirety into the present disclosure.

STATEMENT OF GOVERNMENT INTEREST

This invention was made with government support under Grant No. R01 CA 143050 awarded by National Institutes of Health. The government has certain rights in the invention.

FIELD OF THE INVENTION

The present invention is directed to cone-beam computed tomography (CT) imaging and more particularly to phase-contrast cone-beam CT for such uses as breast imaging.

DESCRIPTION OF RELATED ART

According to the National Cancer Institute, one out of eight women will be diagnosed with breast cancer in her lifetime. And while a reduction in mortality from breast cancer is evident in published reports, each year 40,000 women will die of the disease.

The optimal breast imaging technique detects tumor masses when they are small, preferably less than 10 mm in diameter. It is reported that women with mammographically detected invasive breast carcinoma 1-10 mm in size have a 93% 16-year survival rate. In addition, as the diameter of the tumor at detection decreases, the probability of metastasis declines sharply. If a breast tumor is detected when it is 10 mm or less, the probability of metastasis will be equal to 7.31%. If a 4 mm carcinoma is detected, the metastatic probability will be decreased by more than a factor of 10, to 0.617%.

Although mammography, which on average can detect cancers ~12 mm in size, is the most effective tool for the early detection of breast cancer currently available, mammography has relatively low sensitivity to small breast cancers (under several millimeters). Specificity and the positive predictive value of mammography remain limited owing to structure and tissue overlap. The limited sensitivity and specificity in breast cancer detection of mammography are due to its poor contrast detectability, which is common for all types of projection imaging techniques (projection imaging can only have up to 10% contrast detectability), and mammography initially detects only 65-70% of breast cancers. The sensitivity of mammography is further reduced to as low as 30% in the dense breast. Digital mammography (DM) was developed to try to overcome the limitations inherent in screen-film mammography (SFM) by providing improved contrast resolution and digital image processing; however, a large scale clinical trial, the Digital Mammographic Imaging Screening Trial (DMIST), showed that the rates of false positives for DM and SFM were the same.

The relatively low specificity of mammography leads to biopsy for indeterminate cases, despite the disadvantages of added cost and the stress it imposes on patients. Nearly 80% of the over one million breast biopsies performed annually in the U.S. to evaluate suspicious mammographic findings are benign, burdening patients with excessive anxiety and the healthcare system with tremendous cost. There is a need for more accurate characterization of breast lesions in order to reduce the biopsy rate and the false-positive rate of pre-biopsy mammograms.

To address the mammography limitations as indicated above, one of the inventors has previously developed a cone beam breast CT (CBBCT). Briefly, the major features of the prototype include a horizontal, ergonomically designed patient table with a modular insert to optimize coverage of the uncompressed breast, including the chest wall; wide openings (1 m) on each side of the patient table for easy access to the breast for positioning and potentially good access for imaging-guided biopsy and other procedures without significantly changing the basic platform; and slip-ring technology that facilitates efficient dynamic contrast imaging studies and angiogenesis imaging in the future.

The results of phantom studies indicate that CBBCT can achieve a spatial resolution up to ~2.8 lp/mm, allowing detection of a 2 mm carcinoma and the microcalcifications ~0.2 mm in size for an average size breast (~13 cm in diameter at the chest wall) with a total dose of ~5 mGy. This dose is less than that of a single mammography exam, assuming two views are required for each breast. The image quality of CBBCT for visualizing breast tissues, breast tumors and calcifications is excellent, and coverage of the breast, including the chest wall region, is at least equivalent to mammography. Visualization of major blood vessels is very good without using a contrast agent.

Ultrasound (US) is used diagnostically to distinguish fluid versus solid masses and for localization and biopsy. Lately, it has been investigated with some success to determine benign versus malignant masses through a US exam. US is a low spatial resolution study, has severe limitations in visualizing and characterizing calcifications and is highly dependent on operator skill. Intravenous dynamic contrast enhanced breast MRI (CEBMRI) currently is the only tool that provides functional information to aid in the diagnosis of breast cancer. The CEBMRI study has a high negative predictive value and near 100% sensitivity for invasive breast cancer and serves as a valuable adjunctive modality in managing the breast cancer patient once cancer has been diagnosed by other means. Because it is a tomographic study, it is currently the only breast imaging modality that is FDA approved and can truly be compared to CBBCT. CEBMRI is fully dependent on contrast resolution arising from intravenous contrast agents and the neovasculature associated with tumors. The difference in CEBMRI and all other imaging is that the image reflects contrast enhancement of vasculature rather than the actual breast anatomy. Although CEBMRI has a high sensitivity for invasive cancers, current techniques may be limited in detecting ductal carcinoma in situ (DCIS). CEBMRI is not able to distinguish calcifications and the proposed non-neovasculature involvement with DCIS, which are evident in up to 50% of breast cancers not associated with a mass.

Digital breast tomosynthesis (DBT) presently under development aims to mitigate the effect of overlapping structures. Though a measure of success has been achieved, DBT is fundamentally limited by its constraints in projection geometry; the tomographic slice is not well defined, which can cause a loss of resolution in the axial direction that affects visualization of subtle features, such as amorphous microcalcifications. CBBCT can provide isotropic high-resolution imaging of the entire breast in a more complete tomographic approach compared to other modalities, with without breast compression. It is likely to be of particular value for imaging dense breasts and breasts with implants.

As discussed above, compared to mammography including digital mammography, CBBCT has made significant advancements in detecting breast cancer. However, to accurately characterize breast tumors and calcifications and significantly reduce the biopsy rate and false positive rate of breast biopsy, it is desirable that the CBBCT should achieve a spatial resolution comparable to that of the pathology image, which is the gold standard for breast cancer diagnosis. The requirement of multifold increase in spatial resolution will mandate increasing the radiation dose over 100 times in order to maintain the same contrast-to-noise ratio (CNR) as current CBBCT. For example, if the spatial resolution is required to be increased from 2 lp/mm to 25 lp/mm, to maintain a clinical acceptable CNR, the dose level would be increased from ~6 mGy for an average sized breast with the current CBBCT ~186 times to 1.1 Gy. This dose increase is clinically prohibited.

The following references are considered to provide background information:

1. T Weitkamp, A Diaz, C David, F Pfeiffer, M Stampanoni, P Cloetens and E Ziegler, "X-ray phase imaging with a grating interferometer," Opt. Express 2005; 13(16):6296-6304.

2. G. Faris and R. Byer, "Three-dimensional beam-deflection optical tomography of a supersonic jet," Appl. Opt. 27(24), 5202-5212 (1988).

3. A. Momose, W. Yashiro, S. Harasse, H. Kuwabara, K. Kawabata, "Four-dimensional x-ray phase tomography with Talbot interferometer and white synchrotron light," Proc. SPIE 7804, 780405 (2010).

4. R. A. Kruger and S. J. Riederer, "Basic concept of digital subtraction angiography," Chapter 2, pages 25-26.

SUMMARY OF THE INVENTION

It is therefore an object of the invention to achieve an increase in spatial resolution without increasing the dose to a prohibited level.

It is therefore another object of the invention to substantially reduce the x-ray radiation dose to a patient without reducing spatial resolution and contrast to noise ratio.

It is therefore another object of the invention to achieve mechanically rigid and robust implementation for a rotational-gantry system of phase contrast cone beam CT.

It is therefore another object of the invention to substantially reduce x-ray radiation dose to a patient for grating-based phase contrast cone beam CT imaging.

To achieve the above and other objects, the present invention is directed to a system and method for breast imaging or other purposes (for example, vascular imaging, pediatric cone beam CT, whole body CT imaging and interventional cone beam CT), using spectral x-ray differential phase-contrast cone beam CT that is able to record and present object information in one or more quasi-monochromatic energy channels. X-ray phase contrast cone beam CT and cone beam CT imaging as an emerging new technology will potentially achieve a spatial resolution level up to 25 lp/mm (20 µm voxel size) while maintaining an x-ray dose similar to that of the current CBBCT and mammography. In addition, since x-ray phase contrast imaging is dependent on the principles of refraction and interference of x-ray waves, more subtle information can be detected by retrieving the phase coefficients than that possible with conventional attenuation-based x-ray imaging techniques retrieving attenuation coefficients.

Conventional attenuation-based CT and cone beam CT are quite efficient in distinguishing absorption contrast between soft and hard tissues that have very different linear attenuation coefficients. However, when imaging soft tissues including breast tissues, the low absorption contrast differences of the breast structures (benign and malignant) limit its performance. Phase-contrast techniques are expected to provide an alternative way for soft tissue imaging. Unlike the principle of absorption contrast, phase-contrast imaging originates from the wave nature of x-rays, where refraction and diffraction need to be considered. As an electromagnetic wave, the x-ray is usually characterized by its wavelength, amplitude and phase. When it goes through a medium, its amplitude is attenuated, and its phase is shifted. In x-ray technology, the refraction index n of a material is usually expressed as a complex number $n=1-\delta+i\beta$. The imaginary part $\beta$ contributes to the attenuation of the amplitude, and the real part $\delta$ is responsible for the phase shift. It has been shown theoretically and experimentally that $\delta$ is usually more than $10^3$ times larger than $\beta$. Therefore, a phase contrast imaging technique will potentially provide 1000 times higher object contrast than attenuation-based CT and cone beam CT techniques.

In the past decade, various phase-contrast techniques have been developed to manifest the contrast of $\delta$, almost all of which depend on micro-focus x-ray tubes or synchrotron radiation, which are not practical for widespread clinical applications. Recently, a new phase contrast imaging technique called the differential phase-contrast (DPC) technique has been proposed, which is a grating-based interferometry method. A high power hospital-grade x-ray tube with a wide polychromatic spectrum and high output x-ray power can be used to acquire DPC images. To further reduce the x-ray exposure, we propose a spectral DPC-based cone beam CT (DPC-CBCT) approach. One way is to shape the input x-ray as a quasi-monochromatic spectrum and thus greatly improve the dose utilization efficiency, and another way is to use an energy-resolving detector that can differentiate acquired images in several energy channels. However, it has not previously been used in the context of the present invention. This spectral DPC-CBCT approach is novel over the DPC-CBCT method, and it has not previously been used in the context of the present invention.

Related systems and methods are disclosed in the following U.S. patents: U.S. Provisional Patent Application No. 61/606,562, "Methods and apparatus for differential phase-contrast cone beam CT and hybrid cone beam CT" (Filing date Mar. 5, 2012); U.S. Pat. No. 7,949,095, "Method and apparatus of differential phase-contrast fan beam CT, cone beam CT and hybrid cone beam CT"; U.S. Pat. No. 6,987,831, "Apparatus and method for cone beam volume computed tomography breast imaging"; U.S. Pat. No. 6,618,466, "Apparatus and method for x-ray scatter reduction and correction for fan beam CT and cone beam volume CT"; U.S. Pat. No. 6,504,892, "System and method for cone beam volume computed tomography using circle-plus-multiple-arc orbit"; U.S. Pat. No. 6,480,565 "Apparatus and method for cone beam volume computed tomography breast imaging"; U.S. Pat. No. 6,477,221, "System and method for fast parallel cone beam reconstruction using one or more microprocessors"; U.S. Pat. No. 6,298,110, "Cone beam volume CT angiography imaging system and method"; U.S. Pat. No. 6,075,836, "Method of and system for intravenous volume tomographic digital angiography imaging"; and U.S. Pat. No. 5,999,587, "Method of and system for cone-beam tomography reconstruction," whose disclosures are all incorporated by reference in their entireties into the present disclosure. The techniques disclosed in those patents can be used in conjunction with the techniques disclosed herein.

BRIEF DESCRIPTION OF THE DRAWINGS

Preferred embodiments of the present invention will be set forth in detail with reference to the drawings, in which.

DETAILED DESCRIPTION OF THE PREFERRED EMBODIMENTS

Figure 1A:
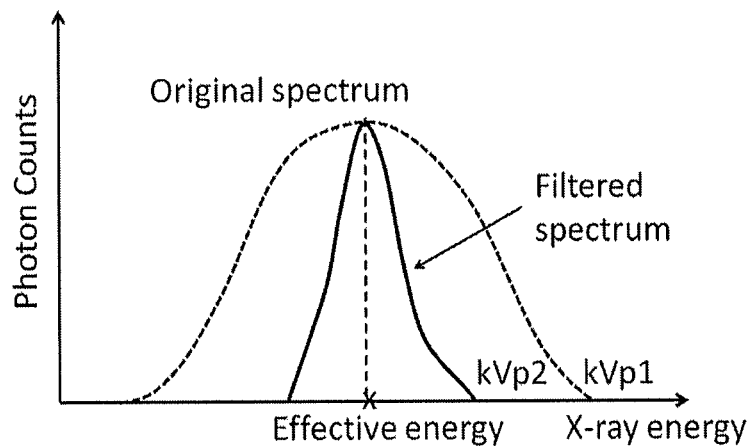
FIGS. 1A-1B are graphs showing the concept of quasi-monochromatic x-ray spectrum.

Preferred embodiments will be set forth in detail with reference to the drawings, in which like reference numerals refer to like elements or steps throughout.

Since the grating-based differential phase contrast (DPC) imaging technique using a hospital-grade x-ray tube was proposed in 2006, researchers have been quickly following up because DPC showed great potential for higher object contrast, which leads to the potential of much higher spatial resolution and dose efficiency than attenuation-based x-ray imaging. However, according to published papers, DPC imaging using a hospital-grade x-ray tube has not yet demonstrated a higher contrast resolution or better dose efficiency as expected than the attenuation-based imaging.

We have developed the DPC technology into DPC-based cone beam CT (DPC-CBCT) technology to provide three-dimensional phase coefficient of an object. According to our preliminary results, the major reason for the unexpected high dose is the polychromaticity when using a hospital-grade x-ray tube. While polychromaticity is not a major concern in absorption-based imaging, it appears as a more severe problem in phase contrast imaging because phase-contrast is much more sensitive to x-ray wavelength. In its early stage, x-ray phase-contrast imaging was limited to monochromatic spectrum by using synchrotrons coupled with single-crystal monochromators. With a polychromatic spectrum, the super-position of interference patterns generated by different x-ray wavelengths will severely degrade or even smear out the fringe contrast.

The introduction of hospital-grade x-ray tubes for grating-based DPC imaging is a smart idea to produce phase contrast using a large focal spot. While such a scheme can tolerate a quite wide x-ray spectrum, it still suffers from polychromaticity. The DPC system can only be optimized for a single x-ray energy, and the grating design and the optical setup are determined based on that 'effective' x-ray energy, which is usually chosen to be the peak energy in the x-ray spectrum. While the x-ray energy deviates from the optimal energy, even though the fringe pattern can still show good contrast, the fringe patterns are displaced by different amounts because the phase shift by the object is different for different x-ray energies, resulting in reduced detection contrast as the fringe patterns are summed up over the spectrum while being detected by the detector. This is similar to the dispersion phenomena in visible light. The low fringe contrast and thus the low contrast-to-noise ratio (CNR) will reduce the contrast and increase noise in the retrieved DPC images and reconstructed DPC-CBCT images. Low CNR will also cause severe phase wrapping in phase retrieval process using either the phase stepping method or the moiré pattern-based method, and if the noise is too high it is very difficult to completely correct the phase wrapping.

A preliminary study was performed through computer simulations to investigate the effect of polychromaticity. It is encouraging to see that by recording and processing DPC-CBCT in different energy channels, just the channel with the optimized energy itself (30 keV in this simulation) can provide similar image quality as that from the whole polychromatic spectrum. So rather than the entire incident x-ray exposure, a small part (40% of photon flux) with the optimal energy can do the same work. Although other non-optimal channels provide inferior image quality, they still provide spectral information of phase coefficient which can help with imaging and characterizing the object.

The simulation gives us two possible directions to improve the dose efficiency and image quality for DPC-CBCT, which leads to the idea of Spectral DPC-CBCT imaging. The first direction is to filter the incident x-ray beam into a quasi-monochromatic spectrum around the effective energy to save a significant amount of dose while producing the same image quality; the second direction is to obtain spectral information of phase coefficients in different energy channels by using a wide polychromatic spectrum to provide more information for imaging and diagnosis.

For the first direction, a quasi-monochromatic spectral can be obtained by appropriately designing the beam filter and selecting x-ray techniques. For a spectrum with a certain width where x-ray photons of all energies contribute to the imaging process, the overall output of such an imaging system, which can be either the attenuation coefficient or the phase coefficient, is usually considered as equivalent to the theoretical value corresponding to an effective energy. The effective energy is usually around the peak of the spectrum. Therefore, for either attenuation-based imaging or phase contrast imaging, it is desired to shape the spectrum as a narrow peak around the effective energy, which is often called a quasi-monochromatic spectrum. To obtain such a quasi-monochromatic spectrum around an effective energy, the following steps should be followed to filter the raw incident x-rays, and the change of spectrum is illustrated in FIG. 1A.

(1) A DPC or DPC-CBCT system is always optimized for a predefined optimal energy, based on which the gratings are fabricated and the optical geometry is set up. Choose this optimal energy as the effective energy for the spectrum.

(2) Prepare a set of metal plates that are made of different materials with different thickness. The materials include, but are not limited to, aluminum, copper, zirconium, molybdenum, tungsten, lead, iron, samarium and etc. The thickness ranges from 0.1 mm to 10 mm. Different material types have different effects in absorbing the low-energy x-ray photons, and thicker plates absorb more x-rays.

(3) Apply a combination of the metal plates to the raw incident x-ray beam and measure the filtered spectrum using a spectrometer. The tube voltage (kVp values) should be adjusted accordingly to shape the spectrum as quasi-monochromatic. The metal plates absorb the low-energy photons in the spectrum and the tube voltage shapes the high energy part. One may start with the aluminum filter with a thickness of 2-3 mm.

(4) Tube current (mA values) and pulse duration (ms values) should then be adjusted to emit sufficient x-ray photons for imaging.

Figure 1B:
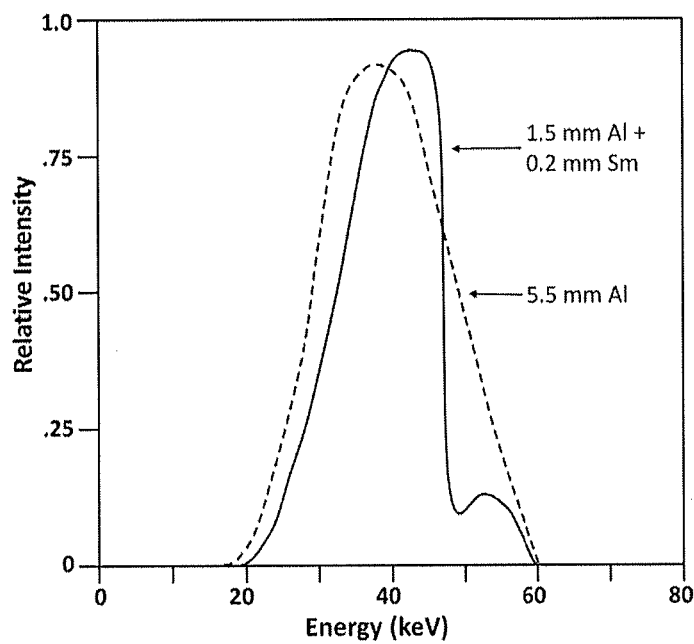

A quick example of spectrum shaping is referred to reference [4], which is also shown in FIG. 1B. If a filter is designed using a 5.5 mm-thick aluminum plate, the x-rays from a tube voltage of 60 kVp can be nicely shaped into a quasi-monochromatic spectrum that is centered at ~36 keV with a half value width of only about 15 keV Another curve in the same figure shows that a 1.5 mm aluminum plate plus a 0.2 mm samarium plate can yield a quasi-monochromatic spectrum for 60 kVp that is centered around 40 keV with a half value width of only 10 keV. According to U.S. Pat. No. 6,480,565 (Ruola Ning, "Apparatus and method for cone beam volume computed tomography breast imaging"), the optimal x-ray energy for tomographic breast imaging is 33-40 keV, which can be readily achieved using the existing beam shaping method. In the present disclosure, the spectrum shaping approach is incorporated in the novel quasi-monochromatic DPC-CBCT imaging technique, especially for breast imaging, to provide better tissue contrast and image quality by manifesting phase contrast around the optimal energy and to reduce radiation dose deposited to a patient. It is also straightforward to know that the quasi-monochromatic spectrum obtained using a beam filter can be readily used for the attenuation-based cone beam CT breast imaging technology (proposed in Ning U.S. Pat. No. 6,480,565) as well to improve tissue contrast, image quality and dose efficiency. In addition, using the same quasi-monochromatic spectrum, both attenuation-based cone beam CT and differential phase contrast cone beam CT can be obtained and combined optimally with the same scans.

For the second direction, an energy-resolving detector should be used that can record the images in different energy channels. A straightforward method is to record intensity images and optimize image processing for different x-ray energy channels. In this way, it can partially remove the "overlapping" of diffraction fringes formed by each quasi-monochromatic component. X-ray energy in each channel can be considered as a "quasi-monochromatic" component of the spectrum if the channel is narrow. For practical considerations, each channel should also be wide enough to contain sufficient x-ray photon flux and to accommodate to energy threshold configurations of the energy-resolving detector. Although compared to regular DPC imaging, each channel will have fewer photons and thus the quantum noise in the recorded intensity images will be higher, the noise level in the DPC image in that channel should not be too high because the fringe contrast, rather than the quantum noise, is the dominant factor in determining the noise level in the retrieved DPC images. Therefore, it is possible to obtain diffraction images, DPC images and DPC-CBCT reconstructions at different energy levels, and the resulting "composite" information can be combined using appropriate algorithms to maximize the final object information by 'coloring' imaging and display. Meanwhile, as image processing is optimized based on the specific x-ray energy in that channel, the performance of each energy channel can be maximized and the utilization of the x-ray dose can be greatly improved.

Figure 2:
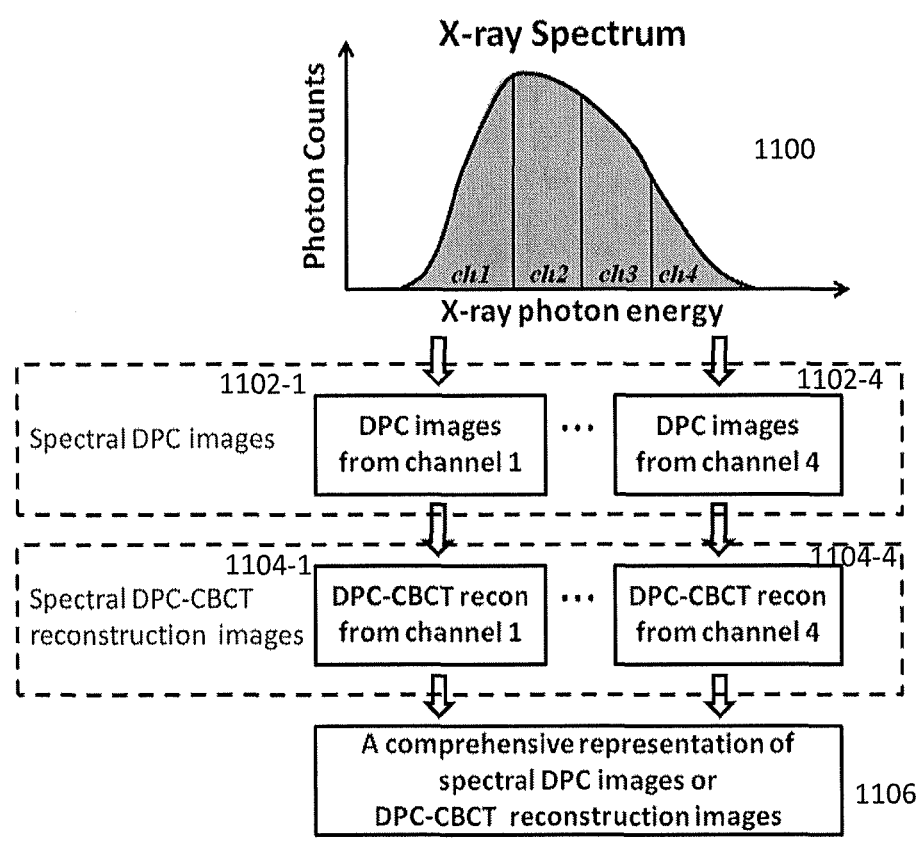
FIG. 2 is a flow chart showing the idea of spectral DPC-CBCT imaging.

The idea of spectral DPC-CBCT imaging is illustrated in FIG. 2. From a four-channel x-ray spectrum 1100, spectral DPC images 1102-1 through 1102-4 from channels 1 through 4, respectively, are taken. From each spectral DPC image 1102-1 through 1102-4, a spectral DPC-CBCT reconstruction image 1104-1 through 1104-4 is reconstructed. From those reconstructed images 1104-1 through 1104-4, a comprehensive representation 1106 of spectral DPC images or DPC-CBCT reconstruction images is formed.

An energy-resolving detector is generally a photon-counting detector, and a good example is Medipix 3, which is the 3rd generation detector in the Medipix family developed by European Center for Nuclear Research (CERN, Geneve, Switzerland). It is a CMOS photon-counting detector that takes images based on the number of particles which hit the pixels when the electronic shutter is open. It has a spectroscopic mode that permits either four separate thresholds (two channels) in simultaneous read/write mode or eight thresholds (four channels) in sequential read/write mode. Medipixel 3 is designed for 5-50 keV, which fits the spectrum used in our DPC-CBCT system. Each Medipix 3 chip has a pitch of 55 μm (no binning), a matrix of 256×256, a dynamic range of 16,000:1 (14 bits) and a total active area of 1.4 cm×1.4 cm. Larger area coverage can be achieved by seamlessly connecting multiple Medipix3 chips by three sides (the only side that is left connects to the readout circuits), which could reach a coverage of 2.8 cm×1.4 n cm (n is an integer), and, given the current nanofabrication technologies, there is no major technical difficulty to enlarge the active area of a single Medipix 3 chip, which could be another possibility to enlarge the active area in the future.

For the purpose of high resolution medical imaging and especially for breast imaging using the proposed spectral DPC-CBCT approach, an energy-resolving detector should be designed and constructed according to the specifications of the existing Medipix3 detector. The major parameters of such a new detector are listed in Table 1.

TABLE 1

Major specifications of a desired energy-resolving detector

| | |
|---|---|
| Detector pitch | 25-1000 μm |
| Spatial resolution | 2.5 lp/mm-25 lp/mm |
| Frame Rate | 0.5 fps-1000 fps |
| Active area | 2.8 cm × 2.8 cm-50 cm × 50 cm |
| Energy response | 5-50 keV |
| Thresholds | at least 8 thresholds per pixel (four energy channels) |
| Dynamic Range | >16,000:1 |

Either the phase stepping method or the moiré pattern method can be combined with the two new directions as described above to perform spectral DPC and spectral DPC-CBCT imaging. The detailed information will be disclosed later in the context of preferred embodiments.

A first preferred embodiment is directed to a quasi-monochromatic differential phase-contrast cone-beam CT system (DPC-CBCT) for in vivo clinical imaging using a quasi-monochromatic spectrum. As shown in FIGS. 3A-3D, such a spectral DPC-CBCT system 100 includes a hospital-grade x-ray tube 102 coupled with a beam filter 103, a source grating 104, a high-resolution detector 110 and a phase-analyzer grating pair 122 mounted on a gantry 112. The beam filter is designed using a combination of metal plates according to the approach described above. It should be noted that the beam filter design is different for a filter that is placed before the source grating and a filter that is placed after the source grating, because the silicon substrate in the grating may also shape the x-ray spectrum to some extent.

The phase stepping method can be used to manifest the phase contrast and to retrieve the phase information, where any of the source grating 104, the phase grating 106 or the analyzer grating 108 can be stepped to apply the phase stepping method.

Figure 3A:
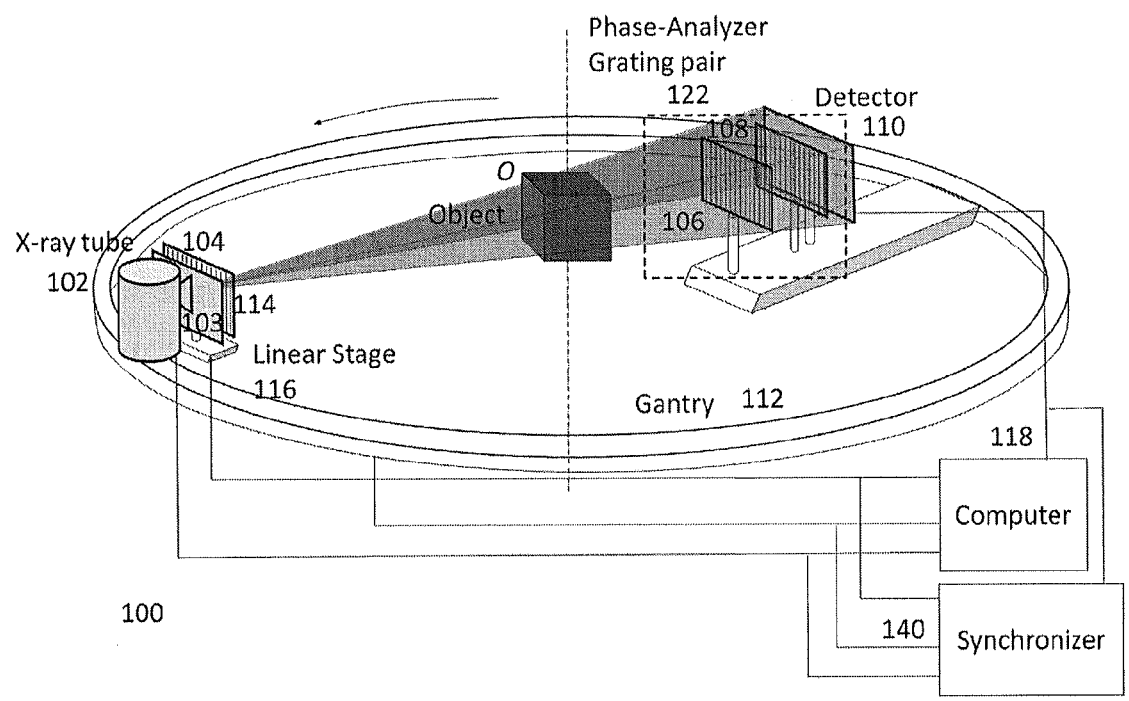
FIGS. 3A-3D are schematic diagrams showing a system according to a first preferred embodiment.
Figure 3B:
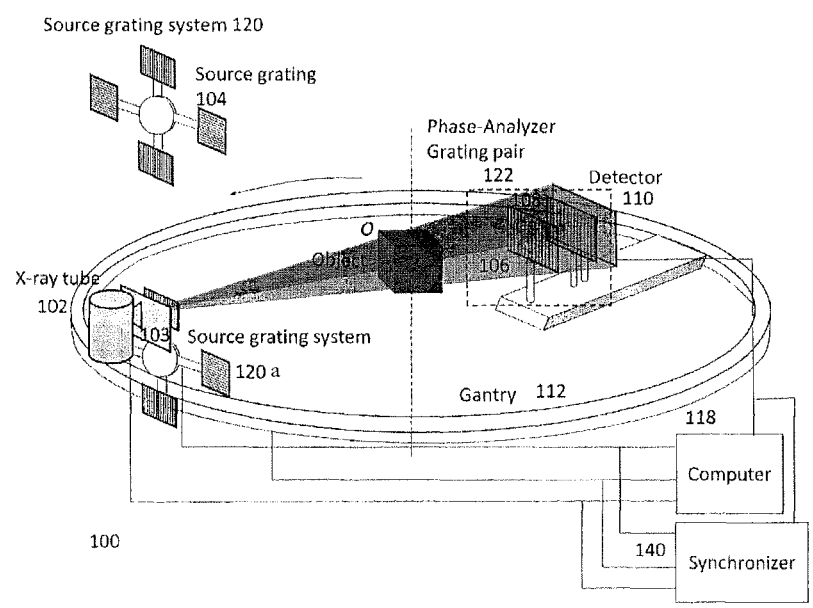

When the source grating 104 is stepped, the stepping mechanism can be designed either as the linear stage-based mechanism in FIG. 3A or the dial source grating system 120 as in FIG. 3B. In FIG. 3A, a motor-driven stage 116 moves the source grating 104 to produce different phase steps. The object O will be kept stationary while the gantry will be rotating to take images during a scan. A computer 118 controls the operations of the system and analyzes the data. For the purpose of high resolution imaging, it is required to accurately synchronize the performance of all the system components. A synchronizer 140 synchronizes the timing of gantry rotation, phase stepping (by linear stage or branch dial), x-ray pulse, and data acquisition to make full use of x-ray exposure for imaging, achieve the required mechanical accuracy and precision and minimize the total scan time. The purpose of the source grating system 120a in FIG. 3B is to produce different phase steps that are defined as relative displacements in the direction perpendicular to grating lines between the source grating 104 and the phase-analyzer grating pair 122 which is composed of a phase grating 106 and an analyzer grating 108. Grating system 120a in FIG. 3B is composed of several branches and at each branch, a source grating is fixed. The grating system is designed in such a way that when each branch is aligned with the phase-analyzer grating pair, the relative displacement between the source grating and the phase-analyzer grating pair ranges from a small fraction of the period of the source grating 104 to one grating period across different branches.

Figure 3C:
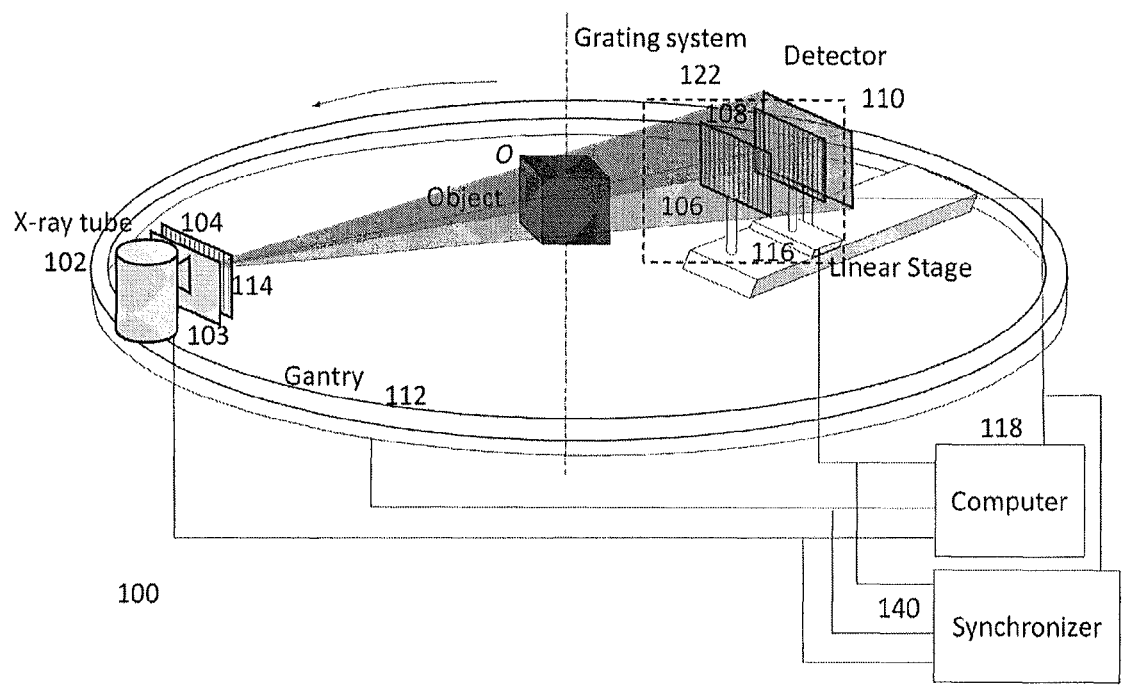
Figure 3D:
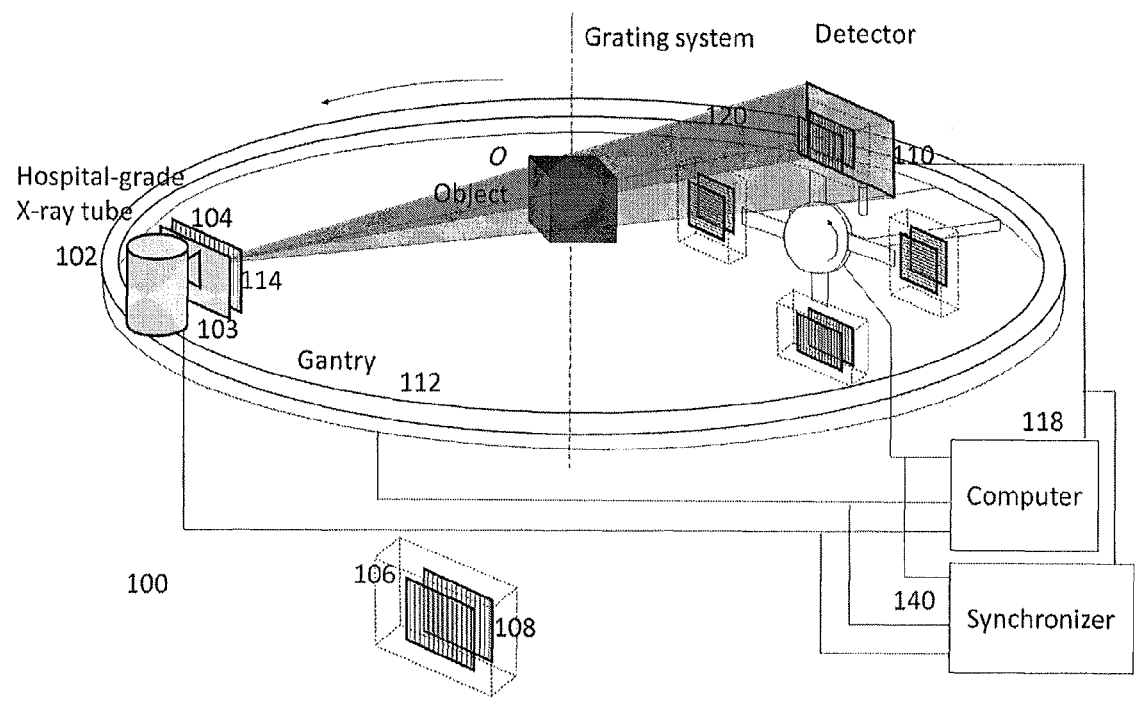

When either the phase grating 106 or the analyzer grating 108 is stepped, the stepping mechanism can be designed either as the linear stage-based mechanism in FIG. 3C or the dial source grating system 120 as in FIG. 3D. The purpose of the grating system is to produce different phase steps that are defined as relative displacements between the phase grating 106 and the analyzer grating 108 in the direction perpendicular to grating lines. In FIG. 3C, the analyzer grating is stepped using a motor-driven linear stage 116 to produce a set of different lateral displacements with respect to the phase grating, and a set of phase stepping images are acquired to retrieve the phase information. Similarly, the linear stage 116 can be also mounted under the phase grating 106 to produce the same effect. In FIG. 3D, the grating system 120 is composed of several branches and at each branch, a phase grating 106 and an analyzer grating 108 are fixed. The relative displacement between the phase grating 106 and the analyzer grating 108 ranges from a small fraction of the period of the analyzer grating 108 to one grating period across different branches. By successively aligning each branch to the optical axis, a set of phase stepping images can be acquired to retrieve the phase information.

A synchronizer 140 control and synchronize the operation of x-ray source, detector, gantry and gratings to perform the imaging process. A computer 118 performs system configuration, data acquisition, three-dimensional tomographic reconstruction and data analysis.

The DPC technique is able to produce one-dimensional or two-dimensional spatial coherence by applying an absorption grating (the source grating 104) to a high power x-ray tube 102 that has a focal spot size of hundreds of microns and a high x-ray output power (>10 kW). The line patterns 114 made of high atomic number materials of the source grating 104 can absorb almost all x-ray photons impinging on them while the grooves in between let all the x-ray photons pass through. The width of the grooves is designed to be comparable to the focal spot size of a micro-focus x-ray tube. Thus the source grating divides a large focal spot x-ray source into several narrow line sources. Each of those line sources is able to produce sufficient spatial coherence at the direction perpendicular to the lines, while they are mutually incoherent. When proper parameters are chosen, those line sources contribute constructively in the imaging process. In a similar manner, the grating pattern can be designed as a matrix of multiple pinholes and each pinhole functions as a point source that is able to individually provide sufficient coherent length in both dimensions but mutually incoherent.

The phase-stepping algorithm [1] is used to calculate each DPC image, the physical principle of which is briefly explained as following: The phase grating 106 shows negligible absorption but substantial phase shift, dividing the x-ray beam into two first diffraction orders. The refracted beams then interfere and form periodical fringes at an integer or fractional Talbot distance where the analyzer grating 108 is placed. The period of the analyzer grating is chosen to be the same as the period of the fringes. If the incident x-ray beam encounters an object before it reaches the phase grating, its wavefront will be perturbed by the object, leading to local displacement of the fringes. The phase stepping algorithm can be used to retrieve the encoded phase information based on detector images. An x-ray detector with a pitch larger than the diffraction fringe period can be used to record the intensity images, which removes the restriction of an ultrahigh detector resolution that has a pitch even smaller than the diffraction fringes. In principle, while any of the three gratings (source grating 104, phase grating 106 and analyzer grating 108) is stepped, the detected intensity value of any pixel in the detector is modulated by the position of the stepped grating. If the modulation function is transformed into the Fourier domain, then the complex angle of the first Fourier component is the first derivative of phase at this pixel. The DPC image of an object acquired in that way is a raw DPC image. Usually the background phase distribution due to the non-uniformity of the grating system is acquired by the same process without an object in place, and the true DPC image of the object is acquired by subtracting the background phase distribution from the raw DPC image.

Figure 4:
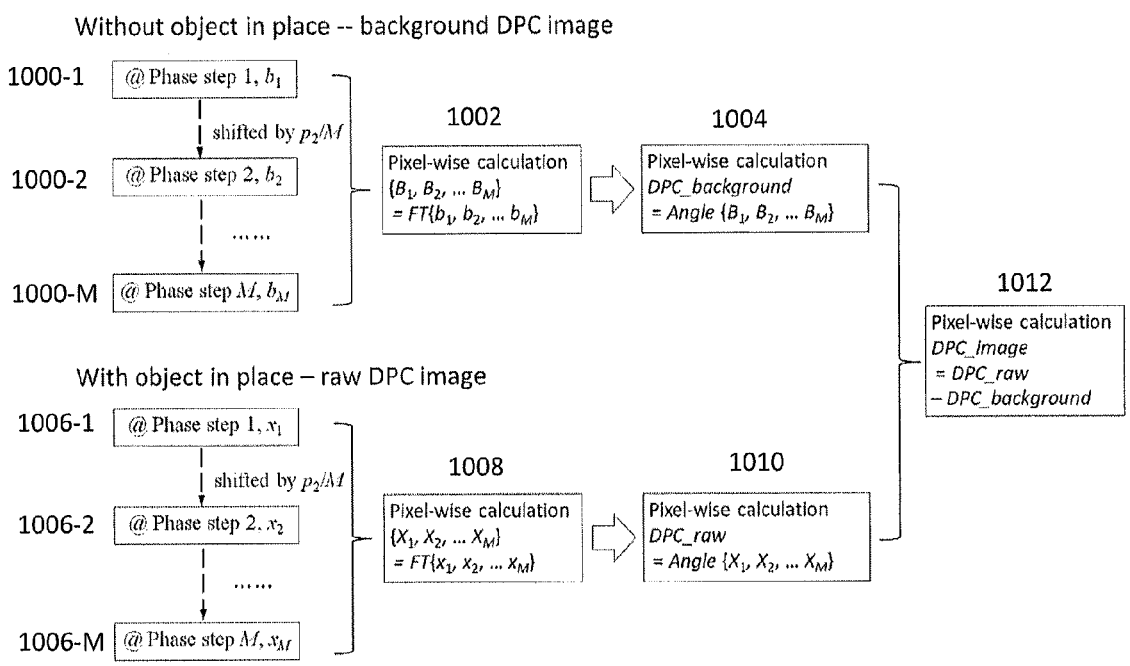
FIG. 4 is a flow chart showing the procedure of the phase-stepping algorithm.

The whole procedure is shown in FIG. 4. Without the object in place, in steps 1000-1 through 1000-M background DPC images are taken at phase steps 1 through M. Pixel-wise calculations are performed in steps 1002 and 1004. With the object in place, in steps 1006-1 through 1006-M, raw DPC images are taken at phase steps 1 through M. Pixel-wise calculations are performed in steps 1008 and 1010. The final pixel-wise calculation in step 1012 calculates the final image from the DPC raw and background images.

It should be noted that the background information can be pre-stored for the background correction for a given DPC system, and therefore it is not necessary to be acquired for every scan. In addition, an attenuation image can be obtained by summing up the phase stepping images to produce absorption contrast, and a dark-field image can be obtained by calculating the ratio of the first Fourier component and the zeroth Fourier component to produce the contrast due to small-angle scattering caused by sub-micron structures.

The DPC images acquired from all view angles will be directly used for reconstruction instead of calculating the line integrals of phase coefficient first from the DPC images. Considering that the cone angle of the DPC-CBCT system is small, the parallel beam approximation can be applied for tomographic reconstruction, and a filtered backprojection (FBP) algorithm with Hilbert filtering can be used [2]. The DPC images are row-wisely filtered using the Hilbert filter, and then are backprojected into the object space to calculate the 3-D distribution of the linear phase coefficient. When the object is fully covered by the x-ray beam at all view angles (no transverse truncation), the reconstruction result is accurate up to a constant. The reconstruction constant can be easily determined by setting the phase coefficient of surrounding air to zero. In the case of volume-of-interest (VOI) imaging where truncation occurs, this reconstruction method also works, but the image quality will be degraded by the background trend, and the reconstruction constant has to be determined using prior knowledge of the object. Besides, backprojection-filtration (BPF) algorithms can be modified for DPC-CBCT reconstruction because a differentiation operation is usually performed before backprojection while the DPC image is very similar to the intermediate result after the differentiation operation. This type of algorithm also has a good capability to handle severe truncations. The procedure of DPC-CBCT imaging using a typical BPF reconstruction comprises the same methods to obtain DPC images, and the only difference is the reconstruction quantity. The major steps are: (a) acquire raw intensity data from all view angles; (b) compute DPC images using the phases-stepping algorithm from the intensity data as shown in FIG. 2; (c) backproject the DPC images to the object space from all view angles; and (d) filter the backprojected data using desired filter(s) along specified direction(s). The projection images can be attenuation images, DPC images and dark-field images, and the reconstructed quantity are then respectively the attenuation coefficient, phase coefficient and density of sub-micron structures.

Figure 5:
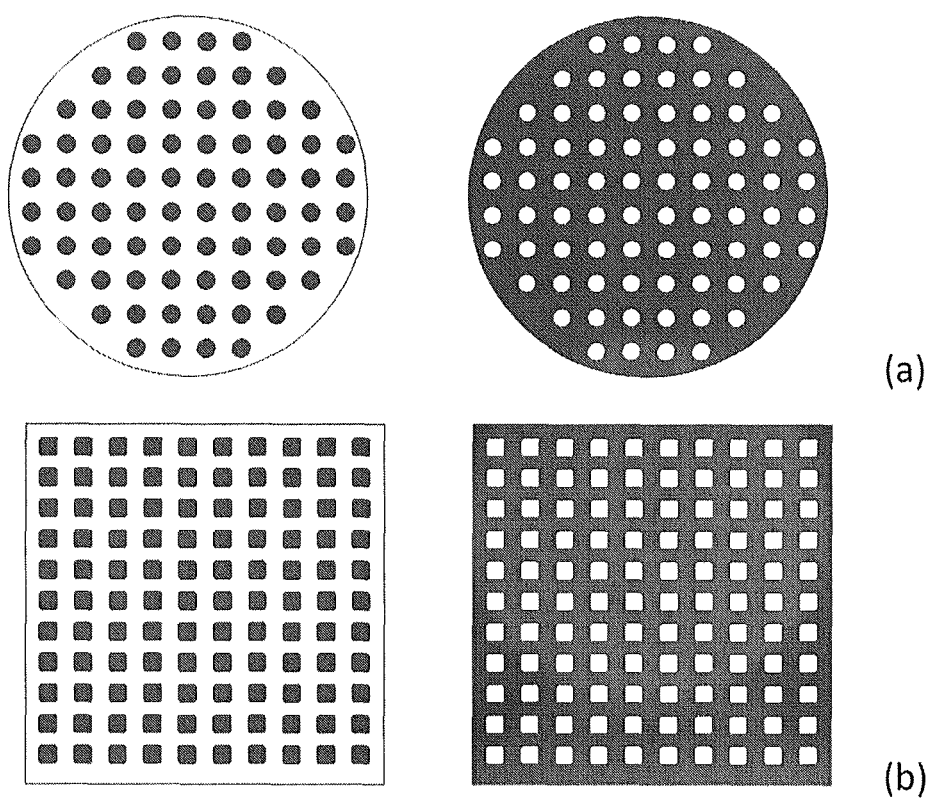
FIGS. 5A and 5B are diagrams showing designs of preferred two-dimensional grating embodiments.

In the present disclosure the one-dimensional grating system with the corresponding scanning protocol and reconstruction algorithm is discussed in detail. It should be noted that it is straightforward to extend the one-dimensional grating system into a two-dimensional system where the source grating is composed of multiple point sources while the phase grating and the analyzer grating are composed of two-dimensional matrices. Some of the possible embodiments are shown in FIGS. 5A and 5B as 1302, 1304, 1306, and 1308. The phase-stepping algorithm should be performed in preferred directions (x, y, diagonal and etc) to extract the phase contrast equally in both x and y directions. A modification should be carried out for the cone beam reconstruction algorithm to deal with the phase gradient in both directions.

Major parameters of the proposed DPC-CBCT system are listed in Table 2. A hospital-grade x-ray is used for the DPC-CBCT system. The x-ray tube has a focal spot size of 0.05 mm to 2 mm and an output power of several kilowatts to tens of kilowatts. It will operate at 10 kVp to 150 kVp. Generally it can be any kind of diagnostic imaging x-ray radiation sources, including mammography tubes, angiography tubes, CT tubes and other general purpose radiographic tubes, depending on the clinical applications.

TABLE 2

Major system parameters

| | |
|---|---|
| Focal spot size | 0.05 mm-2 mm |
| Peak voltage | 10 kVp-150 kVp |
| Detector pixel size | 10 μm-1000 μm |
| Detector frame rate | 0.5 fps-1000 fps |
| Detector dimensions | 3 cm × 3 cm-50 cm × 50 cm |
| Gantry rotation speed | >0.5 RPM |
| Detection Quantum Efficiency (DQE) of detector | >50% |
| Dynamic Range | >30,000:1 |
| The system spatial resolution | >2.5 lp/mm-25 lp/mm |

A two-dimensional detector is used for the DPC-CBCT system. Unlike other phase-contrast imaging techniques, there is no strict requirement for an ultra high resolution detector, and the detector resolution can be ~10 μm-1000 μm, determined by the applications and expected image resolution. The frame rate of the detector is 0.5 frames per second (fps) to 120 fps for different image acquisition protocols. For the potential application of breast imaging which requires high spatial resolution and high contrast resolution, the detector should have a detection quantum efficiency (DQE) of >50% and a dynamic range of >30,000:1. The system spatial resolution is expected to be over 2.5 lp/mm-25 lp/mm.

The source grating is mounted as close to the focal spot as possible for the best field of view. It divides the x-ray beam into many line sources, and the width of each line source is generally less than 50 μM to provide sufficient spatial coherence. The phase grating is mounted right behind the object and yields a phase difference of PI between grooves and ridges. The period of the phase grating is 2 μm to 8 μm. The analyzer grating is mounted right at the surface of the detector, and it attenuates x-rays to 20% to 80% at grooves by strongly attenuation materials. The period of the analyzer grating is the same or half of that of the phase grating (up to a magnification factor which is close to 1.0), depending on the distance between the two gratings, which can be fractional Talbot distances or integer Talbot distances. The distance between the source grating and the phase grating and the distance between the phase grating and the analyzer grating determine the period of the source grating, which is usually 30 μm to 200 μm. The sizes of the gratings are designed to cover the field of view for the specific applications of the DPC-CBCT system. Major grating parameters are listed in Table 3. A possible variation would use two-dimensional phase contrast gratings. It should be noted that such a grating design is ideal for parallel x-ray beam or an x-ray beam with small cone angle as the grating grooves are parallel. When a larger cone angle (>5 deg) is used, it would be better to use focused gratings that are designed and fabricated with consideration of the diverging x-ray beam.

TABLE 3

Major grating parameters

| | Source grating 104 | Phase grating 106 | Analyzer grating 108 |
|---|---|---|---|
| Grating pitch p (μm) | 30-200 | 2-8 | Same or half that for phase grating 106 |
| Groove height t (μm) | 40-200 | 10-50 (phase shift of PI) | 10-100 |
| Duty cycle | Line width <50 μm | 50% | 50% |

The x-ray tube, detector and grating system are mounted on a rotation gantry that can achieve a speed of 0.5 revolutions per minute (RPM) to 60 RPM or larger. The object or patient is kept stationary during a scan.

In the proposed DPC-CBCT technique, the data acquisition geometry is not limited to the circle orbit. The gantry can be controlled and moved by at least one motor to perform scans along various orbits, including a spiral geometry, a circle-plus-line geometry and a circle-plus-arc geometry.

Figure 6:
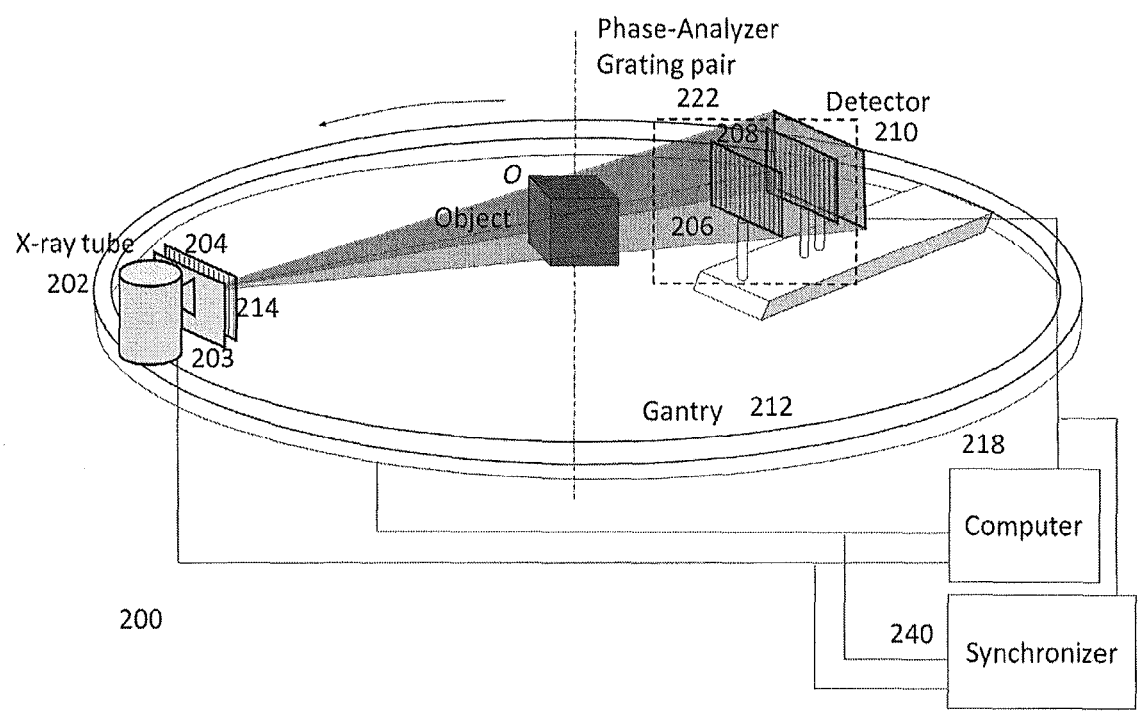
FIG. 6 is a schematic diagram showing a system according to a second preferred embodiment.
Figure 7A:
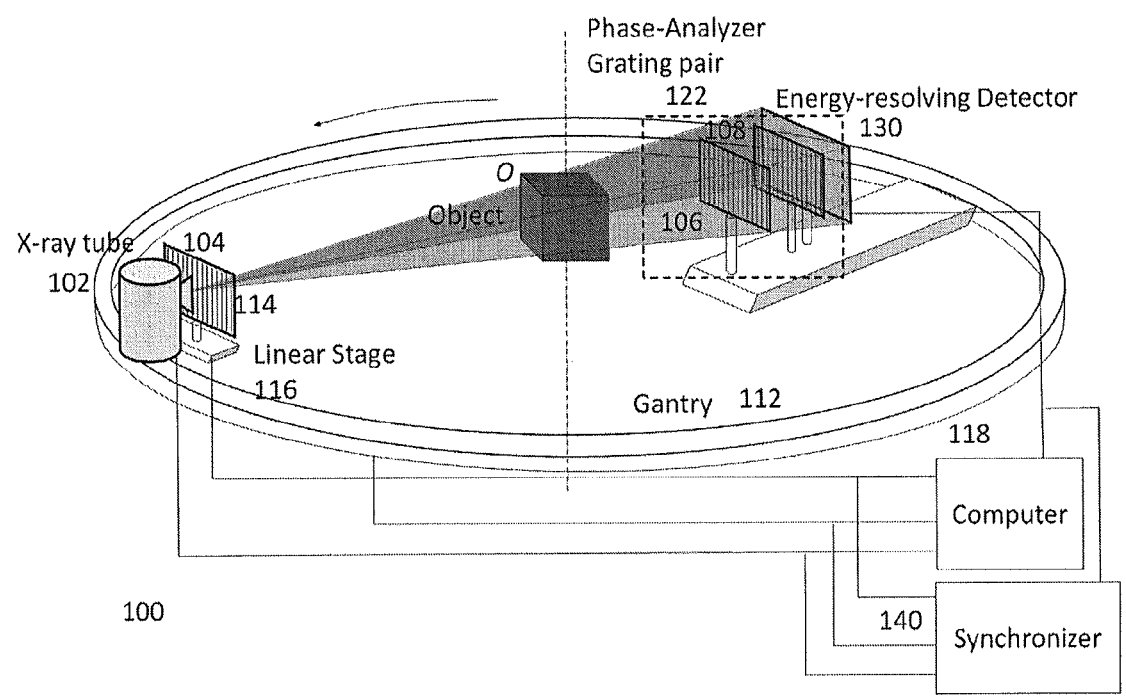
FIGS. 7A-7D are schematic diagrams showing a system according to a third preferred embodiment.
Figure 7B:
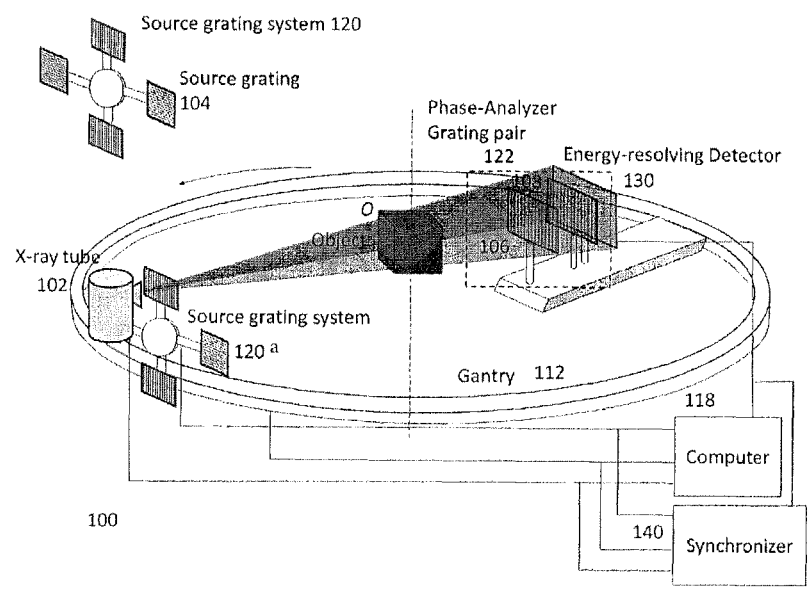
Figure 7C:
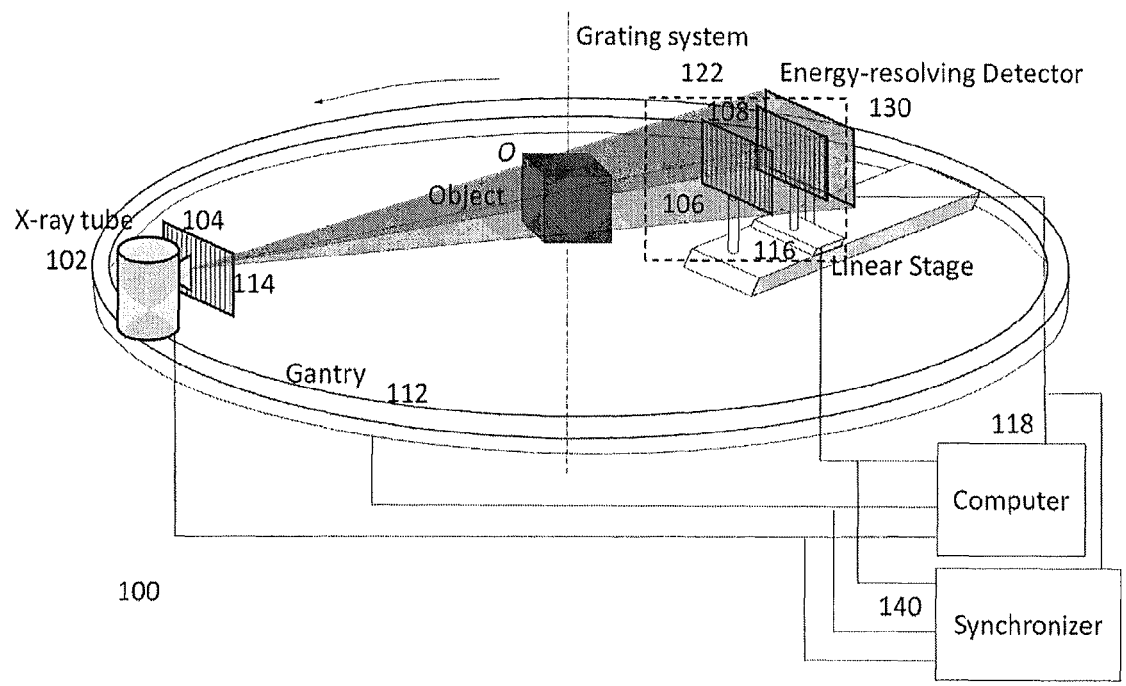
Figure 7D:
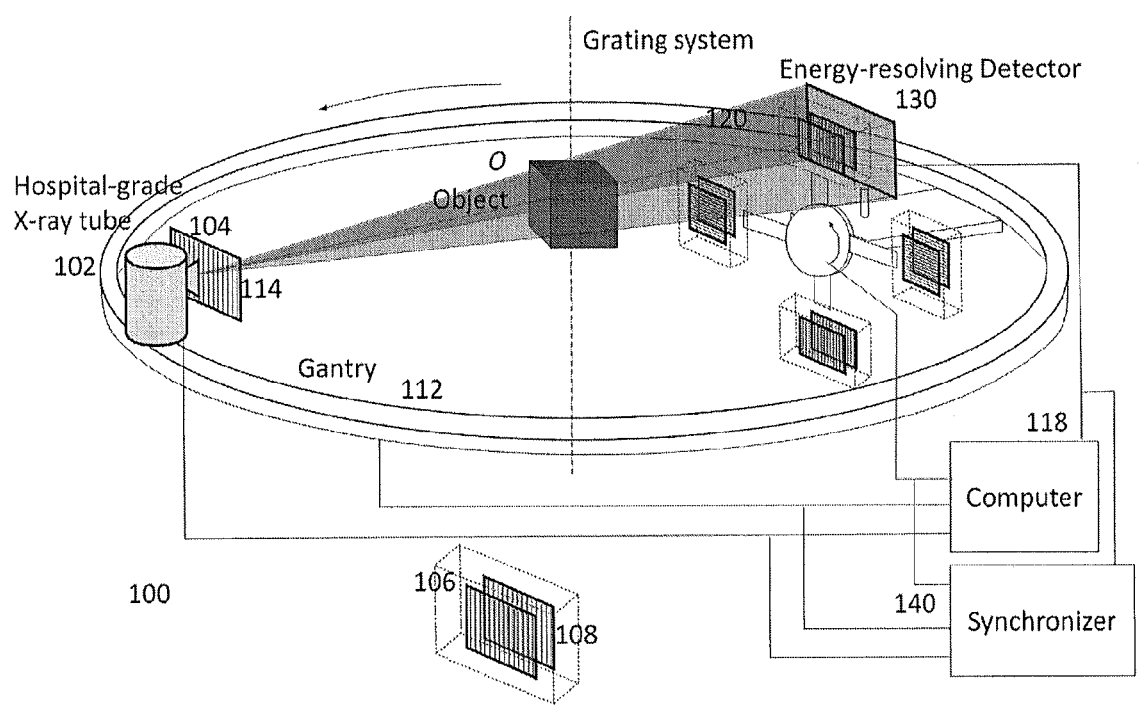

The second preferred embodiment is a variation of the first preferred embodiment where instead of the phase stepping method, the moiré pattern method is used to manifest and retrieve the phase information. The major advantage of the second preferred embodiment s that all the information can be obtained through a single moiré pattern image, and no stepping is required. That reduces the complexity of image formation and makes fast imaging possible. As shown in FIG. 6, the second preferred embodiment has the same system components as that of the first preferred embodiment in FIG. 3A except that the linear stage ix removed. In the system 200, the beam filter 203 is coupled to the x-ray tube to provide quasi-monochromatic x-ray spectrum. The phase grating 206 and analyzer grating 208 are slightly misaligned to produce the moiré pattern, which is distorted with the presence of an object in the x-ray beam as a result of phase change. The embodiment of FIG. 6 includes the following components that are similar to and serving comparable functions to respective components 102, 104, 114, 110, 112, 118, 122, and 140 illustrated in FIG. 3A: X-ray tube 202, source grating 204 with a line pattern 214, detector 210, gantry 212, computer 218, phase-analyzer grating pa 222, and synchronizer 240. By analyzing the moiré pattern using a Fourier transform approach, it is possible to retrieve the attenuation image from the zeroth Fourier component, the differential phase contrast (DPC) image from the first Fourier component and the dark field image from the ratio of the previous two. The reconstruction algorithms as described before can be used to reconstruct the 3D phase coefficient using the retrieved DPC images.

It should be noted that the analyzer grating 208 does not have to be an attenuation grating as that for the second embodiment. Instead, it could be a second phase grating that produces significant phase change but negligible amplitude change. A phase-phase grating pair will also produce similar moiré patterns if the detector is placed at an appropriate location, which could be a fractional Talbot distance or an integer Talbot distance.

The third preferred embodiment is a variation of the first preferred embodiment where the beam filter 103 is removed and the detector is an energy-resolving detector 130. Such a system works in the same way as the first preferred embodiment except that by recording images in different energy channels, it can perform spectral DPC and spectral DPC-CBCT imaging as described in the second direction. This embodiment is shown in FIGS. 7A-7D.

Figure 8:
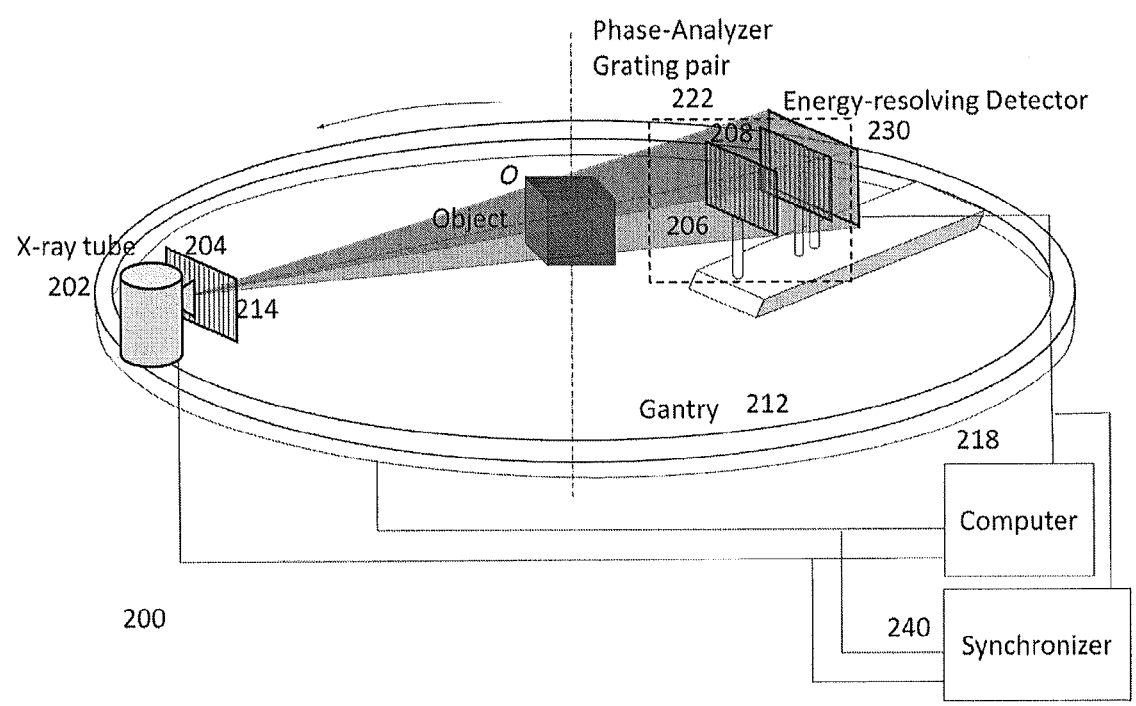
FIG. 8 is a schematic diagram showing a system according to a fourth preferred embodiment.

The fourth preferred embodiment is a variation of the second preferred embodiment where the beam filter is removed and the detector is an energy-resolving detector. Such a system works in the same way as the second preferred embodiment except that by recording images in different energy channels, it can perform spectral DPC and spectral DPC-CBCT imaging as described in the second direction. This embodiment is shown in FIG. 8, and is otherwise similar to the embodiment of FIG. 6 and includes similar components except that the embodiment of FIG. 8 uses energy-resolving detector 230.

The present invention allows the implementation of a DPC-CBCT system to detect and characterize breast tumors and micro-calcifications with a spatial resolution up to 25 lp/mm, which is comparable to that of pathology images and results in the significant reduction of biopsy rate. The following design considerations are involved. The first design consideration is to design and construct a coherent x-ray radiation source that combines the hospital-grade x-ray tube with a specially designed and constructed grating (104) to provide a stable coherent radiation source with 5 cm field of view (FOV) coverage or larger. The second design consideration is to fabricate high quality gratings with uniform microstructures to cover the proposed FOV. The third design consideration is to design and construct an appropriate 2D detector system which has ultra-high spatial resolution (~20 µm/detector cell), a high detective quantum efficiency (DQE), high dynamic range, minimal geometric distortion and excellent linearity. For the third and the fourth embodiments, this detector should also have good energy resolving capability. The fourth design consideration is to develop a practical DPC-CBCT data acquisition scheme along with accurate and efficient phase stepping algorithms and DPC-CBCT reconstruction algorithms. The fifth design consideration is to design and construct the proposed HBCT (hybrid breast CT) system (CBBCT plus DPC-CBCT) to ensure a targeting DPC-CBCT scan and proper coverage of the volume of interest.

As discussed above, the requirement for a phase contrast imaging system is that the incident x-ray beam should be spatially coherent to a certain degree, and it is possible to perform DPC-CBCT imaging using high power hospital-grade x-ray tubes with an attenuation grating. To meet this challenge, we propose to select a high-power mammography tube or general radiography tube with an anode power larger than 10 kW and couple it with a specially designed source grating 104, where the x-ray tube can be considered as being divided into many narrow line sources with width of 10~50 µm, and these line sources are individually spatially coherent in the direction perpendicular to grating grooves but mutually incoherent. With this design, the source is able to provide sufficient x-ray flux even with the strong attenuation of the source grating. The high aspect ratio (the ratio between groove height and groove width) of the grating 104 may affect the field of view, and it is important to mount the grating 104 as close to the focal spot as possible (preferably <1 cm) for larger FOV.

The gratings used for DPC-CBCT imaging will be fabricated using Micro-Electro-Mechanical Systems (MEMS) nanofabrication facilities, including photolithography, physical etching, chemical etching, deposition and electroplating. The major challenge is the high aspect ratio of the gratings (the ratio between groove height and width), which makes etching and electroplating difficult. For the phase grating and the analyzer grating, the aspect ratio can be as high as 15 to 40, which causes difficulties in etching with straight edges or growing gold into deep grooves. To solve this issue, a high-quality <110> orientated single crystal silicon substrate (Nova Electronic Materials, Flower Mound, Tex.) will be used that is highly selective in a preferred direction, with which it is easier to form sharp and deep edges by wet etching using potassium hydroxide (KOH). A nitride layer will be used as the mask and the atomic layer deposition (ALD) will be used to epitaxially grow the seed layer of gold. Next, electroplating will be used to grow the gold layer on top of the seed layer following its own crystal structure. Other elements with high atomic numbers, like Pt, Hf or Ta, can be used as well. Currently the standard large scale MEMS technique is limited to silicon wafers with a diameter of 4 inches, but it is expected to achieve much large silicon wafer size and also grating size in the future. In addition, wafers with small thicknesses will be used to reduce the unnecessary x-ray attenuation of any grating and to reduce the x-ray exposure to patients, Most of the currently available detectors for hard x-rays, including thin film transistor flat panel detector (TFT-FPD), charge-coupled device (CCD) detector, and complementary metal-oxide-semiconductor (CMOS) detector, can be used. Appropriate scintillators should be chosen for the best x-ray energy response. However, for the purpose of breast imaging, which concerns the small size of microcalcifications (as small as 0.2 mm) and low contrast resolution among soft tissues, some special requirements should be specified. The detector should have a dynamic range of >30,000:1 (or >16 bit A/D conversion), a detective quantum efficiency (DQE) of >50% and a spatial resolution of the system should be 2 lp/mm-25 lp/mm. The system can have isotropic spatial resolution. A higher frame rate of 0.5 fps-1000 fps is expected that makes it possible to achieve a faster scanning process and reduced motion artifacts. Besides those features, energy-resolving capability is required for the third and the fourth preferred embodiments. It can be a photon-counting detector that takes images based on the number and energy of particles which hit the pixels according to preset thresholds.

Figure 9:
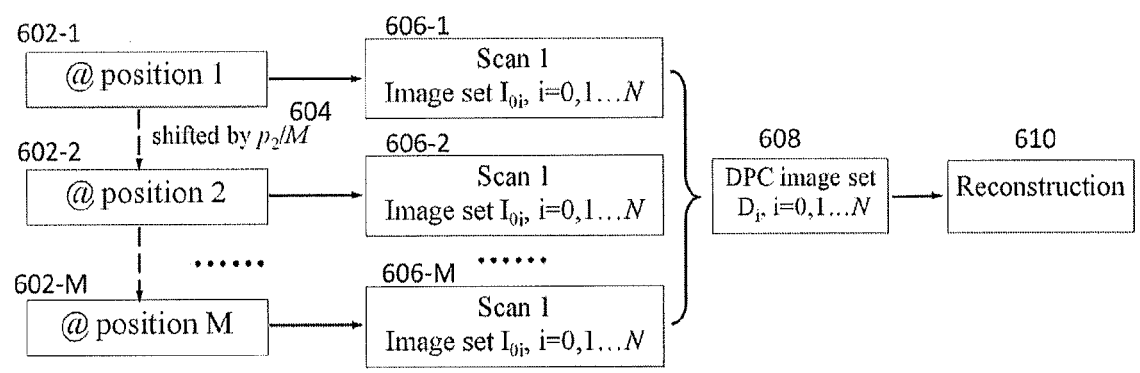
FIG. 9 is a flow chart showing a scanning protocol.

The conventional CBCT scanning protocol is quite straightforward, as only one x-ray exposure is needed to acquire an absorption image at each view angle. The second and the fourth preferred embodiments can perform in the same way as a conventional CBCT scan as no stepping is needed. The first and the third preferred embodiments, however, require at least three x-ray exposures at any view angle, and one of the gratings will be shifted to a different position for each exposure to acquire the phase-stepping images, which will then be processed to compute the final images (attenuation, DPC, or dark-field) at that view angle. Thus the phase-stepping algorithm for phase retrieval adds more complexity in the DPC-CBCT scanning protocols. A straightforward scanning scheme is to use the step-and-shoot method, where all the phase stepping images are acquired sequentially when the gantry stops at each view angle. The gantry rotates and stops at each view angle, and during each stop period, the branch dial grating system rotates to align each branch to the optical axis, the x-ray system shoots and the detector acquires an image. That approach also works for the linear stage-based grating system where the linear stage shifts and aligns the gratings during each stop period. To improve the efficiency, the rising edge of the x-ray pulse should occur immediately after the aligning action is completed by either the branch dial or linear stage which can be precisely controlled by the Synchronizer. This approach can minimize object motion when acquiring the phase stepping images at each view angle, but the total scanning time might be longer because of the step-and-shoot scheme. Another scanning scheme is to divide a complete DPC-CBCT scan into several sub-scans, the branch grating system being rotated to the next branch (FIGS. 3B, 3D, 7B and 7D) or the grating being shifted by the linear stage (FIGS. 3A, 3C, 7A and 7C) before each sub-scan but fixed during each sub-scan. This scheme can reduce the total scanning time because it allows the gantry to continuously rotate. Then the phase-stepping algorithm will be performed to calculate the DPC images at each view angle, and the reconstruction algorithm will be performed to calculate the tomographic images. Assuming that M phase-stepping images (M≥3) are needed to calculate the DPC image at each view angle and N DPC images are needed for tomographic reconstruction, the whole scanning process is illustrated in FIG. 9. The shifted grating (any of the three gratings or the branch grating system) is positioned in a plurality of steps 602-1, 602-2, ..., 602-M in a plurality of positions; between those steps, it is repositioned in step 604. When the shifted grating is in each of the positions, a scanning step 606-1, 606-2, ..., 606-M is performed to take an image set. The scans result in a DPC image set in step 608, which is reconstructed in step 610. Either the FBP-type or iterative-type reconstruction algorithm can be used for reconstruction, and the compressed sensing-based iterative algorithm can be applied to further reduce image noise or reduce required dose while maintaining image quality which is clinically acceptable. Phase wrapping due to large phase derivatives or high noise level in intensity images is the major problem that may cause false phase information in DPC images, appearing as discontinuities. This problem will be solved by detecting singularities based on wavelet analysis and correcting singularities by interpolation.

High precision, good stability and accurate alignment are required in construction and calibration of the DPC-CBCT system, which concern mostly the position of the three gratings that are aligned along the optical axis. They should be mechanically stable down to a scale of approximately one-tenth of its grating period (approximately 3-20 μm). The similar scale of stability also applies to the precision of each step, which can be a rotation or a transverse motion. Another concern is that the relative position of the phase grating and the analyzer grating should be stabilized. The grating mounts will be equipped with precise one-way translation and three-way rotation to make the gratings 106 and 108 well aligned with their grooves parallel to each other, or to make the gratings 206 and 208 misaligned by a desired small angle. The angular sensitivity of grating mounts is expected to be within a couple milliradians to minimize a possible moiré pattern for the phase stepping method or to generate a desired moiré pattern for the moiré pattern method. As the gantry will be rotated during a scan, it is a mechanical challenge to stably rotate the source-detector set while keeping the relative position between the tube, the detector and the grating system unchanged with an accuracy of a few microns.

Large-scale fabrication techniques with silicon wafers are under development that are able to make gratings as large as 30 cm×30 cm. The advance of MEMS techniques may also make it possible to make two dimensional gratings that are able to show phase contrast equally well in both directions and eliminate the possible problems with object orientation. There are no major technical obstacles in fabrication of large-area (up to 50 cm×50 cm), high-resolution (>25 lp/mm) detectors using CMOS or CCD techniques, and the frame rate is expected to be improved by tens of times with novel parallel acquisition and fast caching techniques. Hence, the field of view will be greatly enlarged for ultrahigh resolution breast imaging or whole body imaging. Though the x-ray tube is not a limitation for DPC imaging, emerging techniques of compact micro-focus x-ray tubes, including laser plasma tubes and liquid metal target tubes will further improve image resolution and simplify the system design by removing the grating 104 that may increase field of view and improve exposure uniformity.

With the technique advances described above, the spectral DPC-CBCT imaging system is expected to scan faster (achieve a few seconds/scan), cover larger objects, and provide higher spatial resolution, which makes it possible to use the DPC-CBCT imaging as both screening and diagnosis tools. The screening DPC-CBCT system will be designed with a lower spatial resolution (~100-75 μm) and the patient will be exposed with very low exposure (lower than that of two view screening mammography). The diagnostic DPC-CBCT system will be designed with a higher spatial resolution (~50-20 μm) and the patient dose will be equivalent to that of a diagnostic mammography (~6 mGy for average size normal density breast). Currently the VOI breast imaging is designed as a hybrid system with two sub-systems: a CBCT system and a DPC-CBCT system. In the future it can be further simplified as a single DPC-CBCT imaging system that can perform both a screening scan and a diagnostic VOI scan by switching the field of view, different resolutions (standard resolution for large field view and screening imaging and ultrahigh resolution for small field and diagnostic imaging) and different readout rates (0.5 frame/s-120 frame/second).

Our first application of the proposed DPC-CBCT technique is a cone beam breast CT modality for breast cancer diagnosis to reduce the biopsy rate; however, the technology can be also used for whole body imaging as well as angiography and bone imaging.

Figure 10A:
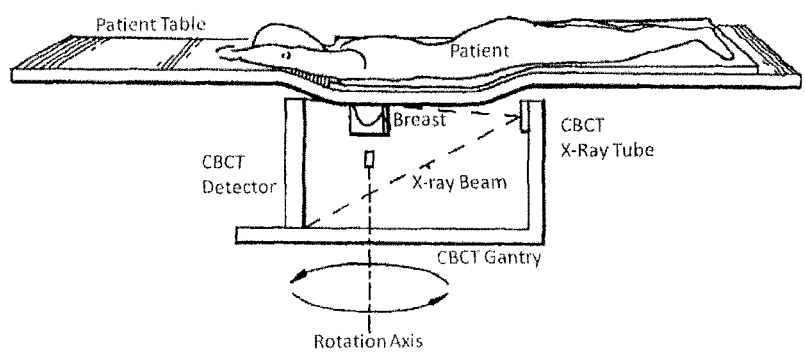
FIGS. 10A-10E are schematic diagrams showing a system according to a fifth preferred embodiment.
Figure 10B:
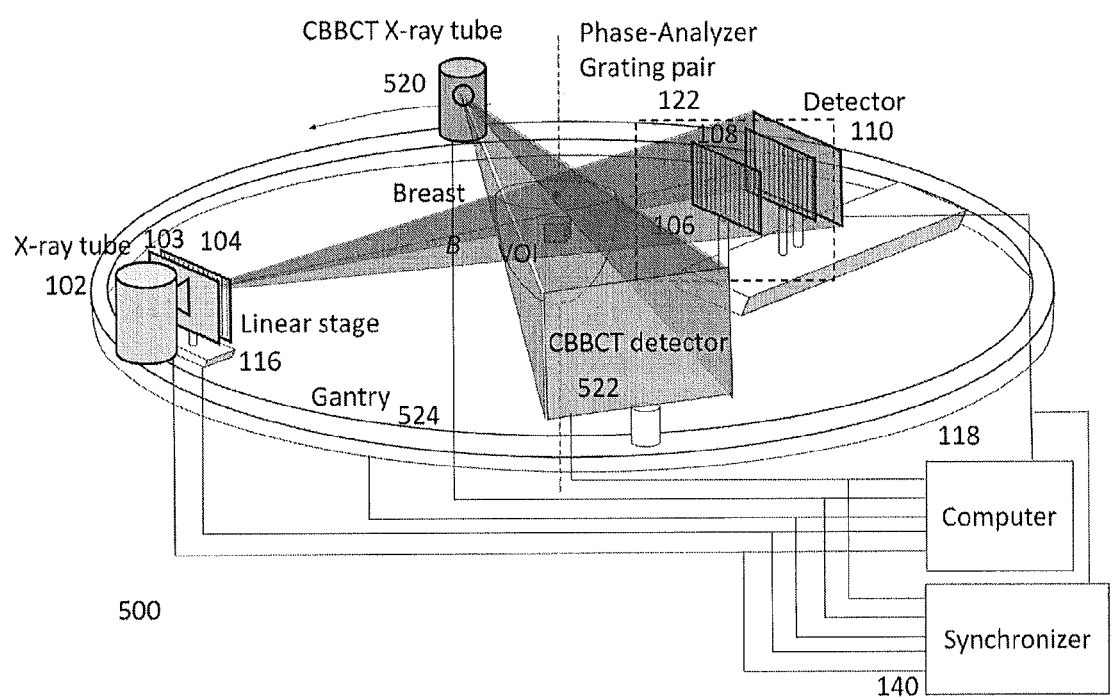
Figure 10C:
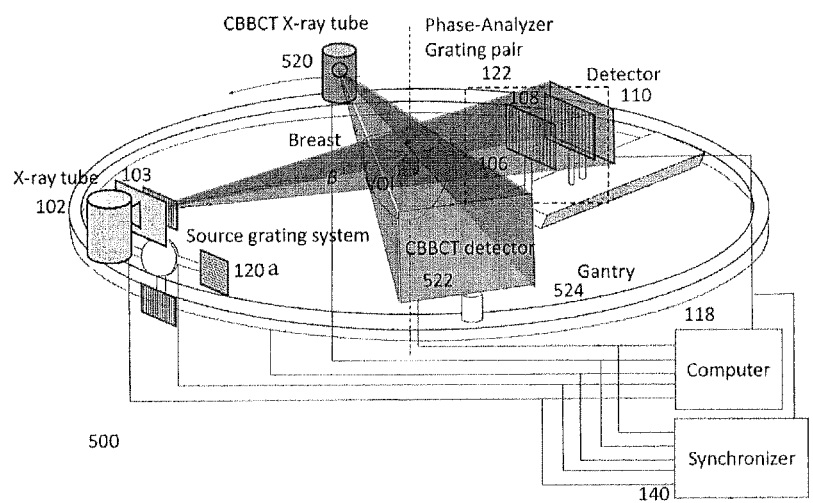
Figure 10D:
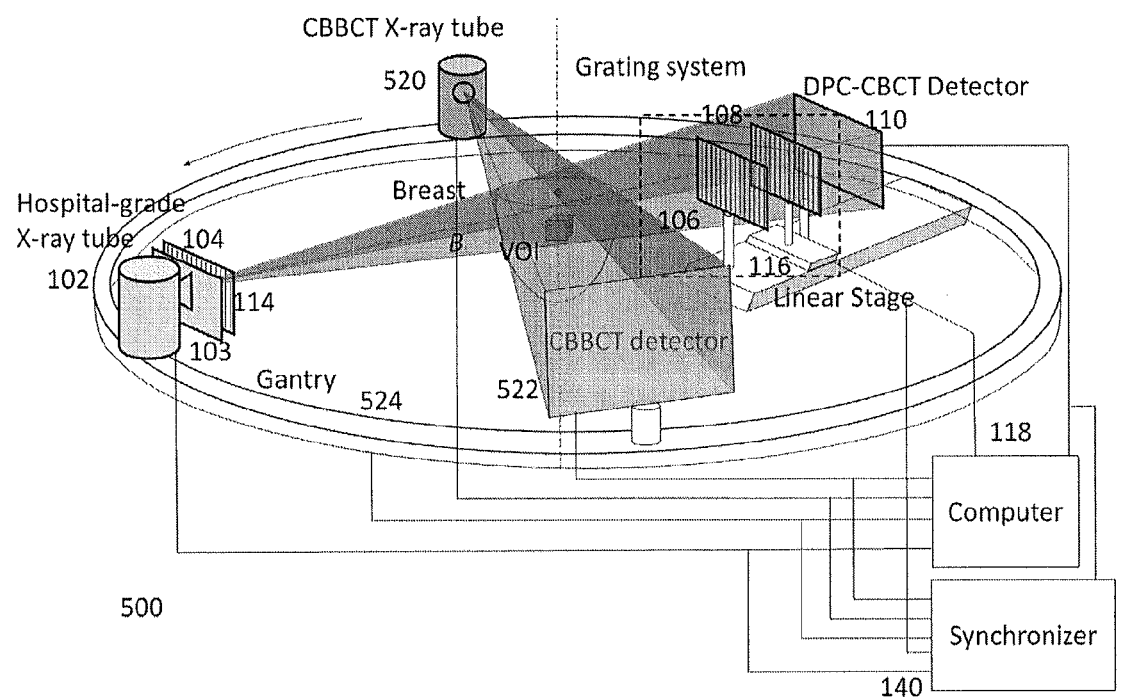
Figure 10E:
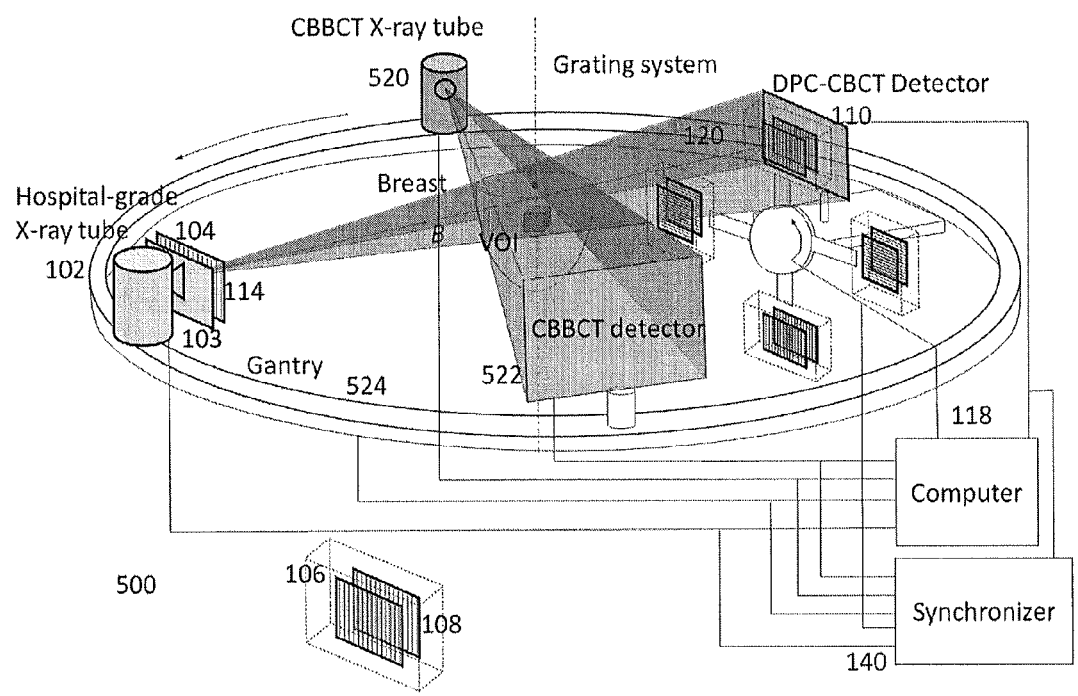

A fifth preferred embodiment combines current cone beam CT with spectral DPC cone beam CT to form a hybrid cone beam CT that is capable of acquiring both 3D high resolution cone beam CT imaging and ultrahigh resolution DPC-conebeam CT imaging. FIG. 10A shows the cone beam CT breast imaging system as disclosed in U.S. Pat. No. 6,480,565 "Apparatus and method for cone beam volume computed tomography breast imaging" (Ning '565), and the hybrid cone beam CT system is supposed to replace the cone beam CT system beneath the patient table to perform hybrid breast imaging. FIGS. 10B, 10C, 10D and 10E show one possible design for a hybrid cone-beam CT system 500 for breast imaging by combining the first preferred embodiment with the cone beam CT technology. The system 500 includes a current cone beam breast CT (CBBCT) system, which is mainly composed of an x-ray tube 520 and a flat-panel detector 522 such that the CBBCT imaging chain images the breast only using a half-cone geometry in which x-ray radiation radiates the breast only without penetrating chest cavity or other body parts of the patient, resulting in substantially reduced radiation to the patient. On the same rotary gantry 524, a quasi-monochromatic DPC-CBCT system is constructed which is one of the four sub-types of the first preferred embodiments as shown in FIG. 3B-3E. The CBBCT is used to scan the whole breast B first and find out the 3D location of any suspicious volume; the breast is then translated and positioned such that the suspicious volume is centered in the field of view (FOV) of the DPC-CBCT system; finally the DPC-CBCT system performs an ultrahigh-resolution scan of a region of interest (ROI), and the phase coefficient of the 3D volume is reconstructed. This ultrahigh-resolution DPC-CBCT scan is expected to reveal ducts (<0.25 mm in width), small vessels (<0.5 mm in width) and microcalcifications (<0.2 mm in diameter) for diagnosis and treatment of breast cancers.

It is also straightforward to apply the beam filter to the attenuation-based CBCT imaging chain in the hybrid system to further improve tissue contrast, image quality and dose efficiency for CBCT.

Studies have shown that while DPC-CBCT outperforms in most cases, attenuation-based CBCT is more sensitive in imaging certain materials and soft tissues. Therefore, the hybrid system can utilize the advantages of both DPC-CBCT and attenuation-based CBCT to provide complimentary information in medical imaging and breast imaging. In addition, using the same quasi-monochromatic spectrum in the hybrid system, both attenuation-based cone beam CT and differential phase contrast cone beam CT can be obtained and combined optimally with the same scans.

Figure 11A:
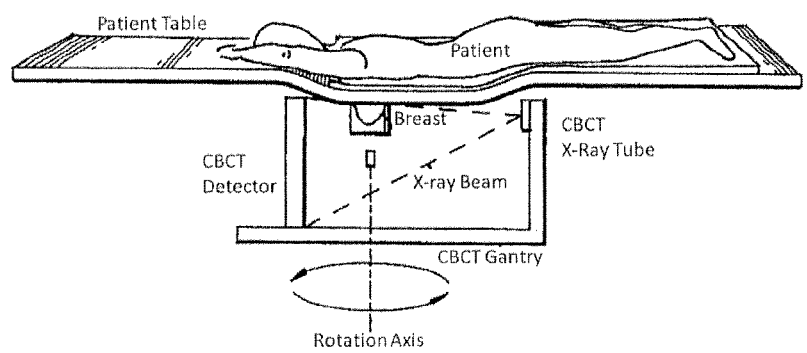
FIGS. 11A and 11B are schematic diagrams showing a system according to a sixth preferred embodiment.
Figure 11B:
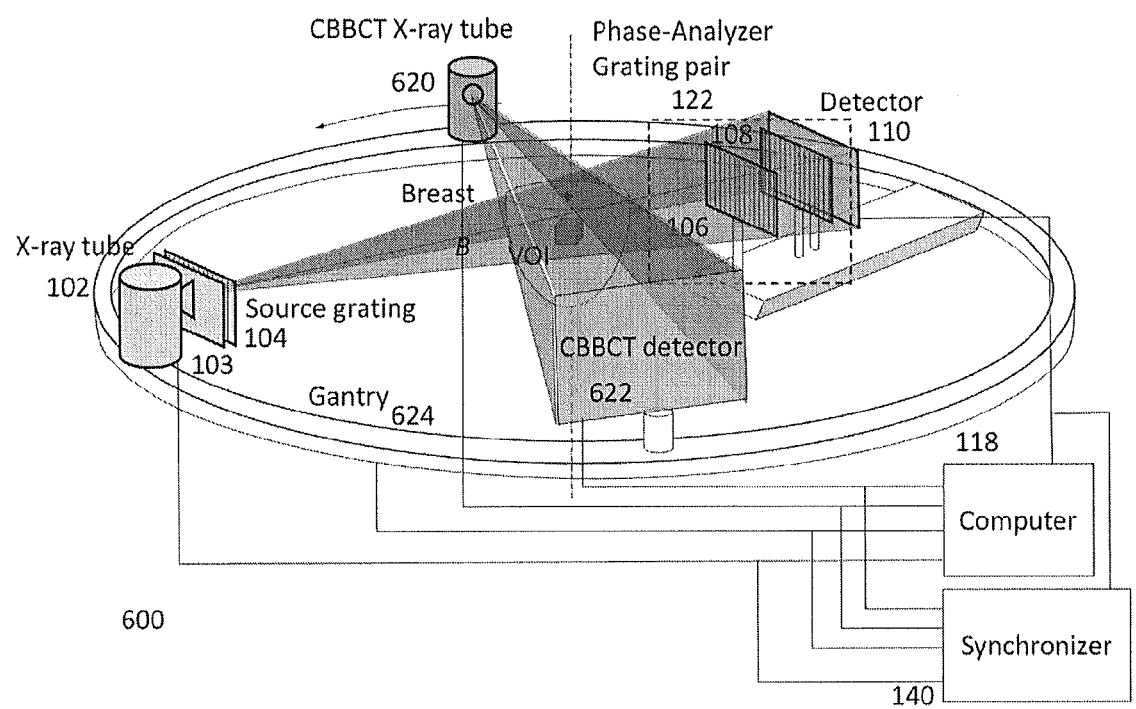

The sixth preferred embodiment is a variation of the hybrid system as shown in FIGS. 11A and 11B. FIG. 11A shows the cone beam CT breast imaging system as disclosed in U.S. Pat. No. 6,480,565 "Apparatus and method for cone beam volume computed tomography breast imaging" (Ning '565), and the hybrid cone beam CT system is supposed to replace the cone beam CT system beneath the patient table to perform hybrid breast imaging. FIG. 11B is actually a combination of the moiré pattern-based system (second preferred embodiment) and the current CBBCT system. CBBCT system images the breast only using a half-cone geometry in which x-ray radiation radiates the breast only without penetrating chest cavity or other body parts of the patient, resulting in substantially reduced radiation to the patent. It should be noted that as no stepping is required in the system 600, it can perform fast data acquisition, which makes dynamic imaging possible using this system. As illustrated, the embodiment 600 of FIG. 11B includes CBBT X-ray tube 620 and CBBT detector 622, and gantry 624 serving similar functions as respective components 102, 122, and 524 in FIG. 10B.

Figure 12A:
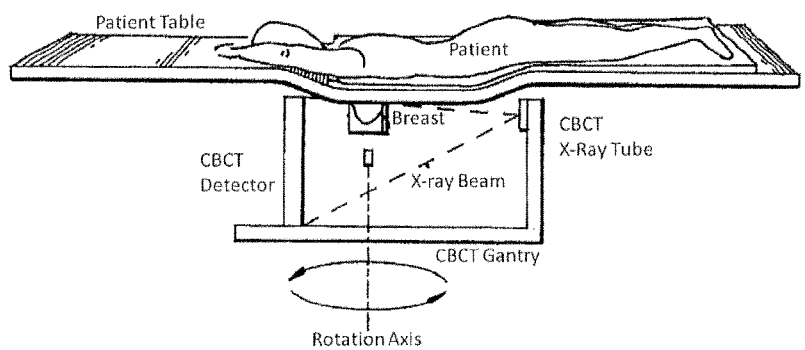
FIGS. 12A-12E are schematic diagrams showing a system according to a seventh preferred embodiment.
Figure 12B:
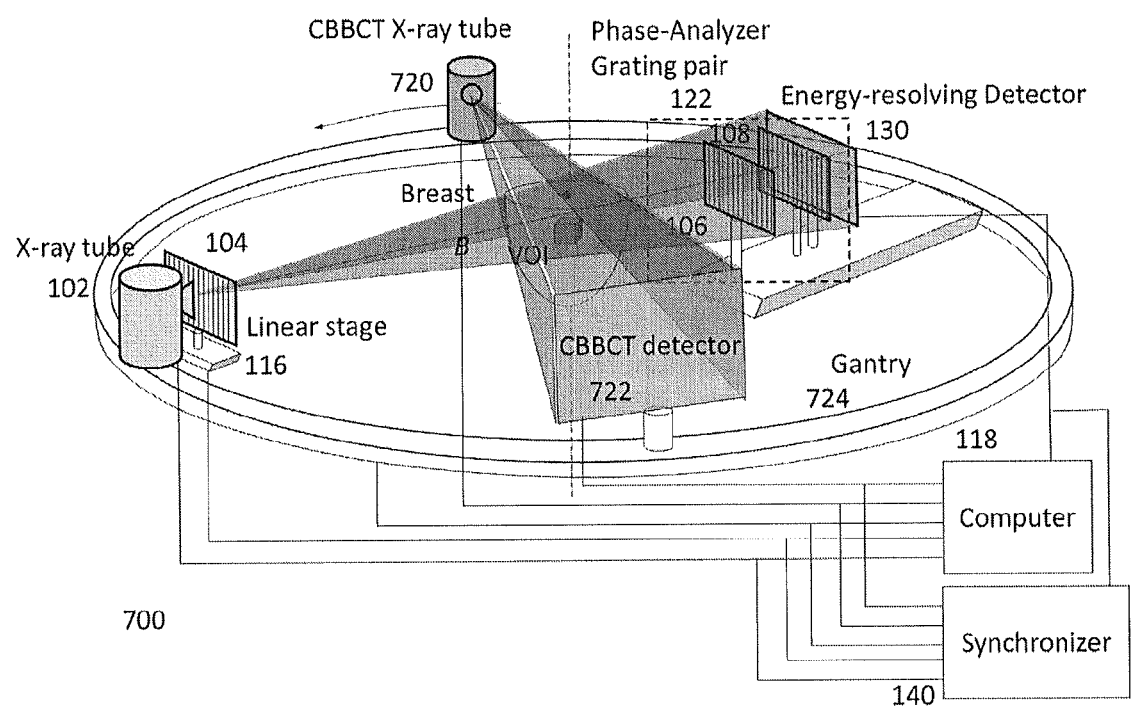
Figure 12C:
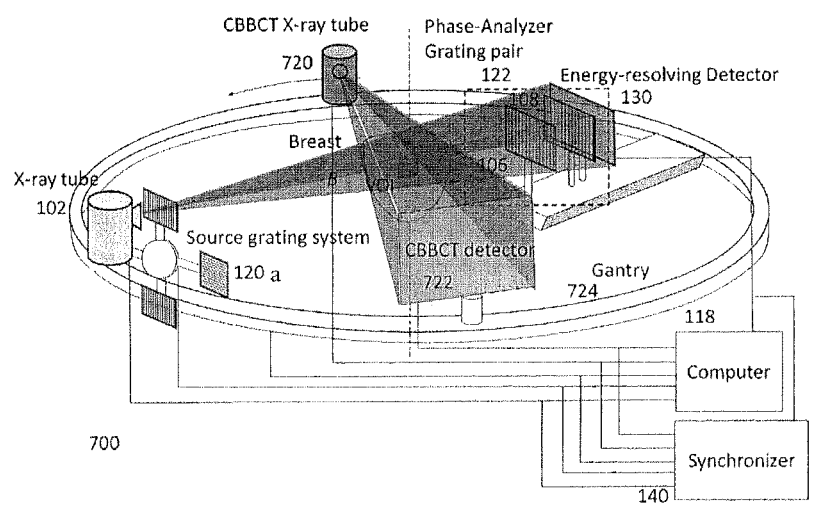
Figure 12D:
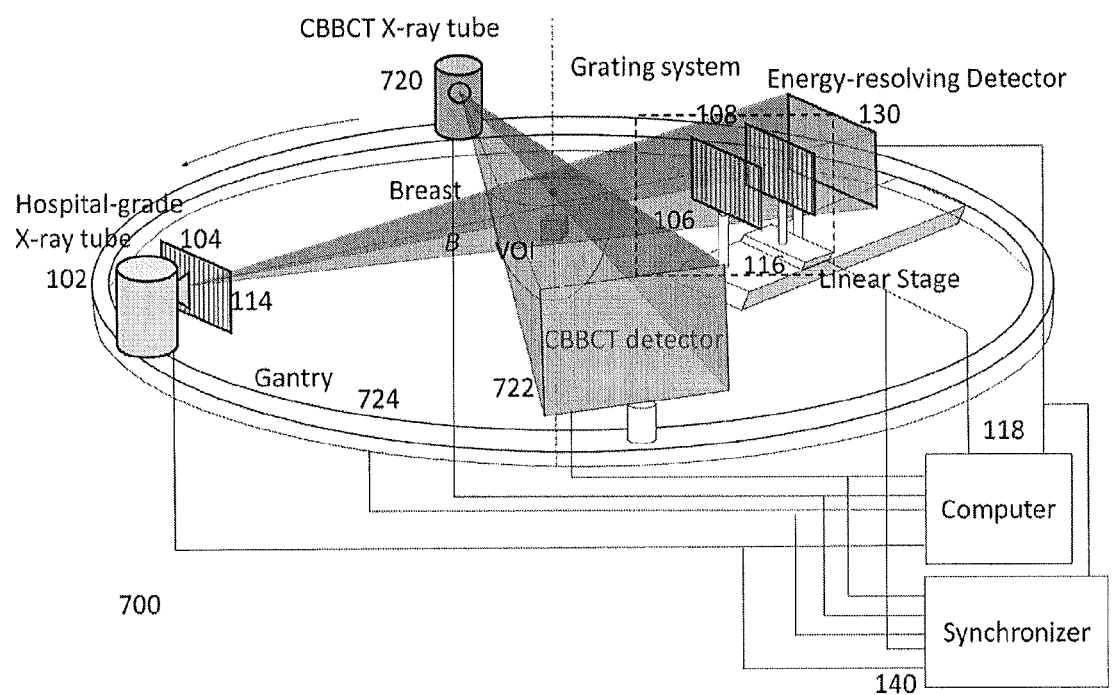
Figure 12E:
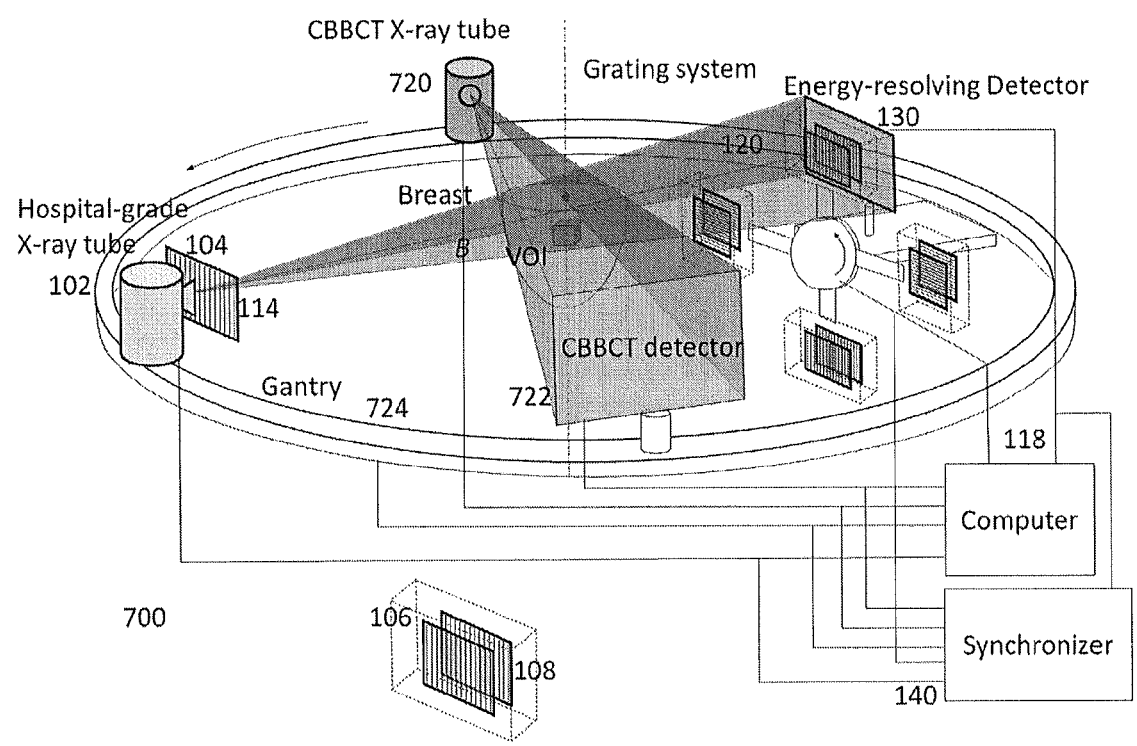

The seventh preferred embodiment is a variation of the hybrid system as shown in FIGS. 12A-12E. FIG. 12A shows the cone beam CT breast imaging system as disclosed in U.S. Pat. No. 6,480,565 "Apparatus and method for cone beam volume computed tomography breast imaging" (Ning '565), and the hybrid cone beam CT system is supposed to replace the cone beam CT system beneath the patient table to perform hybrid breast imaging. FIGS. 12B, 12C, 12D and 12F are actually combinations of the phase stepping-based spectral DPC-CBCT system using an energy-resolving detector (the third preferred embodiment) and the current CBBCT system. As illustrated, the seventh preferred embodiment 700 includes CBBT X-ray tube 720 and CBBT detector 722, and gantry 724. The CBBCT system images the breast only using a half-cone geometry in which x-ray radiation radiates the breast only without penetrating chest cavity or other body parts of the patient, resulting in substantially reduced radiation to the patient.

Figure 13A:
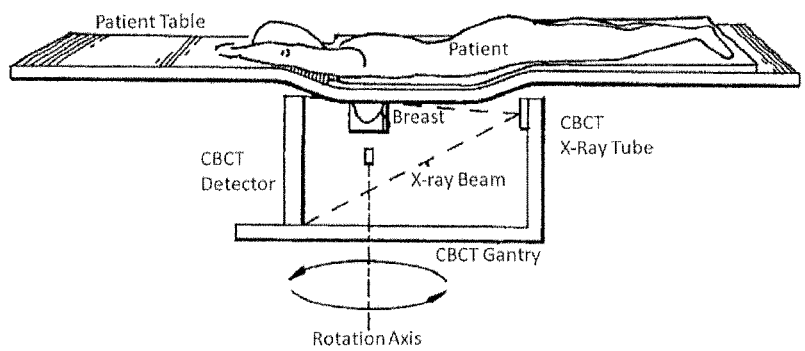
FIGS. 13A and 13B are schematic diagrams showing a system according to an eighth preferred embodiment.
Figure 13B:
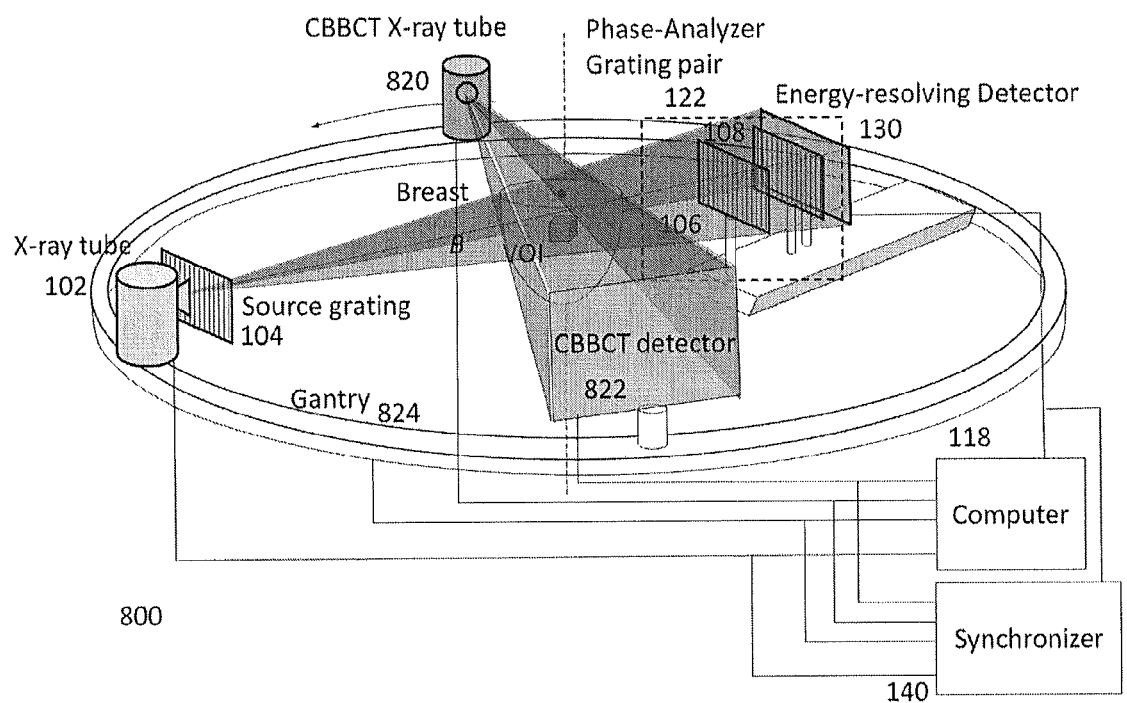

The eighth preferred embodiment is a variation of the hybrid system as shown in FIGS. 13A and 13B. FIG. 13A shows the cone beam CT breast imaging system as disclosed in U.S. Pat. No. 6,480,565 "Apparatus and method for cone beam volume computed tomography breast imaging" (Ning '565), and the hybrid cone beam CT system is supposed to replace the cone beam CT system beneath the patient table to perform hybrid breast imaging. FIG. 13B is actually a combination of the moiré pattern-based spectral DPC-CBCT system using an energy-resolving detector (the fourth preferred embodiment) and the current CBBCT system. As illustrated, the eight preferred embodiment 800 includes CBBT X-ray tube 820 and CBBT detector 822, and gantry 824. The CBBCT system images the breast only using a half-cone geometry in which x-ray radiation radiates the breast only without penetrating chest cavity or other body parts of the patient, resulting in substantially reduced radiation to the patient.

It should be noted that all the eight embodiments can be performed in a spiral scan mode to increase the coverage by moving the object along the rotation axis while the gantry is rotating. There are no theoretical or mechanical difficulties for this application extension.

The mathematical model of DPC imaging using a polychromatic spectrum will now be discussed. To model a polychromatic imaging process, the final intensity image should be integrated over the entire imaging process. The complex amplitude for a specific wavelength $\lambda$ is expressed in Equation (1), and the diffraction image using a polychromatic spectrum is shown in Equation (2). The notations include $U_0$ for the incident complex amplitude, U for the complex amplitude at the detector plane, $T_{obj}$ for the transmission matrix of object, $T_{G1}$ for the transmission matrix of the phase grating, $T_{G2}$ for the transmission matrix of the analyzer grating, H for the Fresnel kernel and I for the intensity imaging acquired by the detector. Major simulation parameters are listed in Table 4.

$$U(\lambda,x,y)=(U_0(\lambda,x,y)\cdot T_{obj}(\lambda,x,y)\cdot T_{G1}(\lambda,x,y)\otimes H(R;\lambda x, y)\cdot T_{G2}(x,y) \quad (1)$$

$$I(x,y)=\int (U(\lambda,x,y)\cdot U^*(\lambda,x,y)d\lambda \quad (2)$$

TABLE 4

Simulation parameter selection

| | |
|---|---|
| Source-to-Object distance | 1.0 m |
| Detector pitch | 64 μm |
| Phase grating pitch | 4 μm |
| Analyzer grating pitch | 2 μm |
| Number of phase steps | 4 |
| Basic simulation unit | 0.5 μm |
| Number of projections | 360 |

As the Medipix 3 allows eight thresholds to define four channels in its spectroscopic mode, we assume the x-ray spectrum is divided into four channels and each channel contains a certain percentage of the total incident x-ray photons. Each channel is represented using its center energy, including 20 keV (20%), 30 keV (40%), 40V (25%) and 45 keV (15%). The optical setup of the DPC-CBCT system is optimized for 30 keV.

Figure 14:
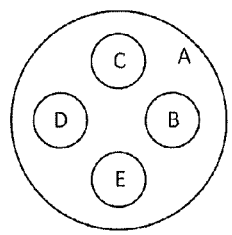
FIG. 14 is a diagram showing a phantom used in simulation.

The phantom is composed of a water cylinder (8 mm in diameter) with four rod inserts (2 mm in diameter). The layout is shown in FIG. 14, and the coefficients are listed in Table 5. For convenience, the assigned phase coefficients are normalized to the phase coefficients of water at 30 keV, which is $3.7175\times 10^4$ m$^{-1}$ according to the NIST database and the Klein-Nishina formula.

TABLE 5

Phase coefficients for the numerical phantom
(normalized to the phase coefficient of water at 30 keV)

| | A (water) | B | C | D | E |
|---|---|---|---|---|---|
| 20 keV | 1.20 | 1.26 | 1.32 | 1.38 | 1.44 |
| 30 keV | 1.00 | 1.05 | 1.10 | 1.15 | 1.20 |
| 40 keV | 0.90 | 0.945 | 0.99 | 1.035 | 1.08 |
| 45 keV | 0.80 | 0.84 | 0.88 | 0.92 | 0.96 |

For fair comparison, the reconstruction is expressed in "CT Numbers" that is defined in a similar way as that for attenuation-based CT. The phase coefficient of water is the theoretical number as defined in the simulation, and the CT number for each energy channel is calculated using the phase coefficient of water for that energy channel. The expression is shown as Equation (3).

$$CTNumber = 1000 \times \frac{\varphi - \varphi_{water}}{\varphi_{water}} \quad (3)$$

Figure 15A:
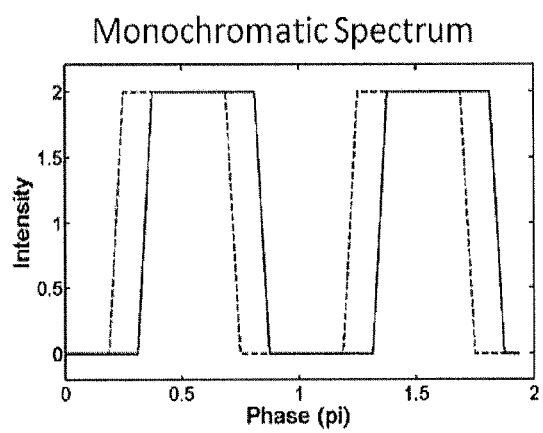
FIGS. 15A and 15B are graphs showing the difference between monochromatic and polychromatic spectra in interference fringe images.
Figure 15B:
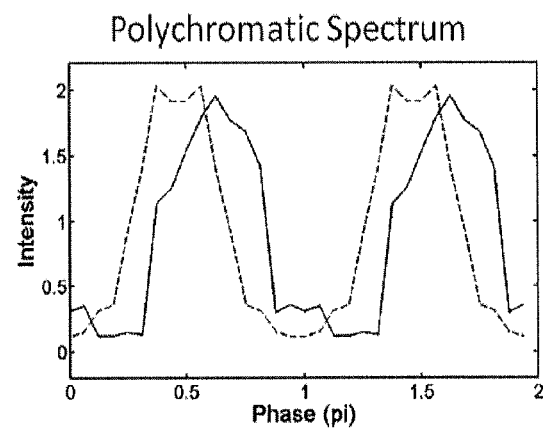

FIGS. 15A and 15B demonstrate the difference between a monochromatic spectrum and a polychromatic spectrum for DPC imaging. Both figures are profiles of fringe displacement in a self image due to phase shift of an object, where the incident x-rays have a unit intensity. The monochromatic spectrum has an energy of 30 keV, while the polychromatic spectrum is designed as above. Assume the phase shift is $0.0625\pi$ for 20 keV, $0.125\pi$ for 30 keV, $0.1875\pi$ for 40 keV and $0.25\pi$ for 45 keV due to their different wavelength and phase coefficients. The normalized contrast of monochromatic fringes is close to 2.0 (2.0 vs. 0) while the contrast of polychromatic fringes is averagely 1.3 (1.6 vs. 0.3), which is 35% lower and thus more vulnerable to noise and phase wrapping. It is obvious that the shape of the polychromatic fringe is no longer a square wave, and the shape is significantly changed after phase shift (dispersion). While using eight steps for phase stepping, the calculated phase shift is $0.125\pi\pm 0.002\pi$ for the monochromatic spectrum and $0.142\pi\pm 0.047\pi$ for the polychromatic spectrum, where the uncertainty is about 30% due to dispersion. That is another source of noise in the retrieved DPC images.

In experiments we cannot directly observe the fringe contrast of a self-image. Instead, we can estimate the fringe contrast from the phase-stepping images acquired at each phase step because the background intensity represents a point on the solid curve in FIGS. 15A and 15B. Such a contrast is only 1.20 vs. 0.70 (normalized) for our bench-top system. Despite the imperfectness of gratings, the low fringe contrast due to polychromaticity is a major reason why the actual x-ray dose is much higher than expected.

DPC-CBCT imaging process was simulated for each energy channel using the numerical phantom as described above to produce a series of spectral DPC-CBCT reconstructions. A polychromatic DPC-CBCT reconstruction was also simulated by summing up all the energy channels after Fresnel diffraction, as suggested by Equations (1) and (2).

Figure 16A:
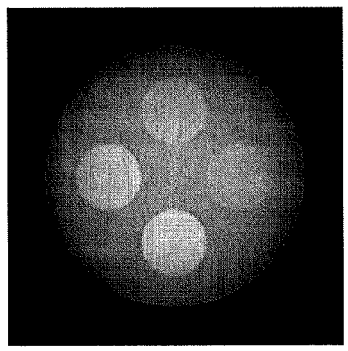
FIGS. 16A-16E are reconstructed images of the phantom for four energy channels and the combined spectrum.
Figure 16B:
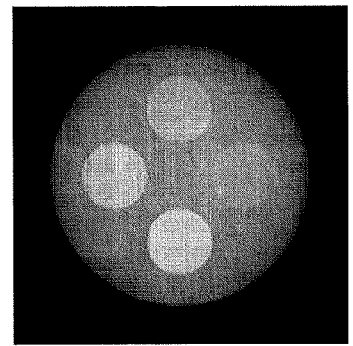
Figure 16C:
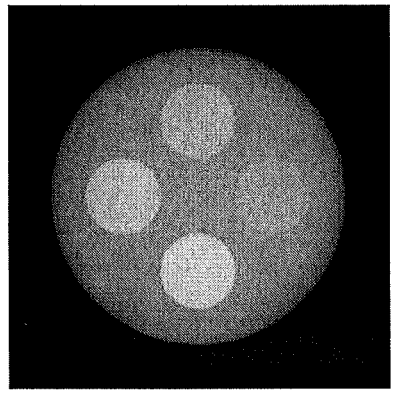
Figure 16D:
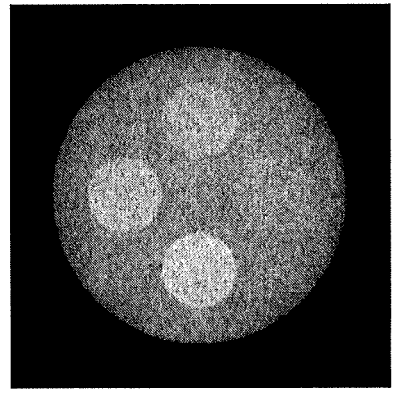
Figure 16E:
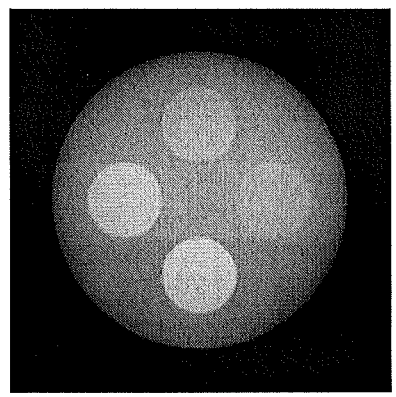

The reconstructed axial images are shown in FIGS. 16A-16E. FIG. 16A-16D are reconstructions from four energy channels, which are respectively 20 keV, 30 keV, 40 keV and 45 keV. FIG. 16E is the reconstruction using the combined polychromatic spectrum. Judging by visual inspection, the four spectral DPC-CBCT reconstructions show different noise levels, uniformity and contrast levels. The reconstruction at 30 keV, which is the optimal energy, looks comparable to that from the polychromatic DPC-CBCT reconstruction.

The measured central noise level, uniformity and contrasts of the four inserts are listed in Table 6 in the unit of CT Numbers (CTN). It should be noted that at 30 keV, where the system is optimized, the channel is able to provide the lowest noise level and the highest object contrast, and the overall image quality is similar to that for the polychromatic DPC-CBCT using the entire spectrum. While other energy channels provide sub-optimal noise and contrast, they still provide significant information of the energy response of the phase coefficient for each insert, which directly leads to a potential "coloring" representation of objects and helps improved diagnostic efficiency and accuracy.

TABLE 6

Image quality comparison of spectral
DPC-CBCT and polychromatic DPC-CBCT

| | Spectral DPC-CBCT | | | | Polychromatic |
|---|---|---|---|---|---|
| | 20 keV | 30 keV | 40 keV | 45 keV | DPC-CBCT |
| Uniformity (CTN) | 163 | 40 | 52 | 44 | 46 |
| Noise (CTN) | 12 | 8 | 17 | 43 | 9 |
| Contrast (B) (CTN) | 46 | 52 | 43 | 37 | 50 |

TABLE 6-continued

Image quality comparison of spectral
DPC-CBCT and polychromatic DPC-CBCT

|  | Spectral DPC-CBCT | | | | Polychromatic DPC-CBCT |
| --- | --- | --- | --- | --- | --- |
|  | 20 keV | 30 keV | 40 keV | 45 keV |  |
| Contrast (C) (CTN) | 96 | 108 | 85 | 77 | 104 |
| Contrast (D) (CTN) | 137 | 148 | 131 | 128 | 142 |
| Contrast (E) (CTN) | 184 | 192 | 172 | 167 | 187 |

Figure 17A:
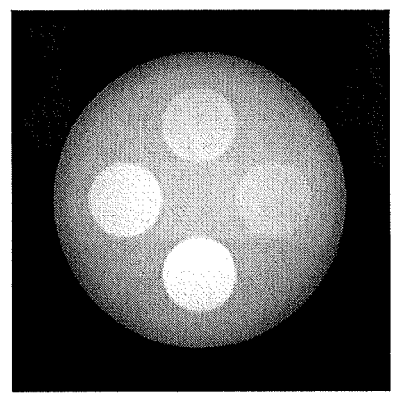
FIGS. 17A and 17B are reconstructed final grayscale images.
Figure 17B:
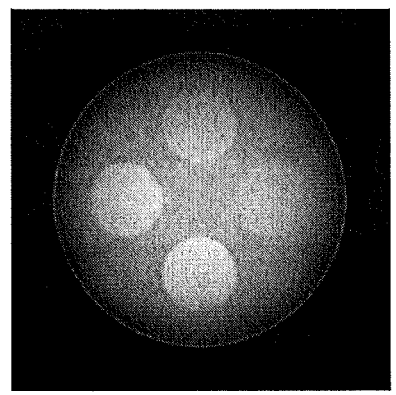

How to use and represent the multi-folded spectral information is another interesting topic for spectral imaging. For example, material decomposition is used for dual-energy CT to utilize the spectral information. For spectral DPC-CBCT imaging, a straightforward approach is to weight and sum up the reconstruction images obtained from all energy channels and to display the final images in conventional gray scales. FIGS. 17A and 17B show two examples of this representation. FIG. 17A is the weighted average by the inverse of reconstruction noise using (1/12, 1/8, 1/17, 0) where 12 CTN, 8 CTN and 17 CTN are the reconstruction noise at channel 20 keV, 30 keV and 40 keV. The purpose of this type of average is to reduce the noise in the final image, which is now only 6 CTN. FIG. 17B is the subtraction of the DPC-CBCT reconstructions from 30 keV and 40 keV, and thus the weighting coefficients are (0, 1, −1, 0). The purpose of this type of average is to enhance the difference of phase coefficients between certain energy channels.

Figure 18:
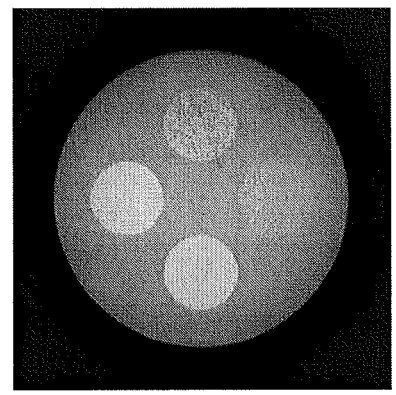
FIG. 18 is a reconstructed image using a color representation.

An alternative coloring representation approach is proposed that displays an object using a color map, where each color component (Red, Green and Blue) is defined as the weighted sum of composite object information. For example, if there are four energy channels and the phase coefficients computed for each channel is $\phi_1$, $\phi_2$, and $\phi_4$, the RGB components can be are defined in Equation (4):

$$(R, G, B)^T = W \cdot (\phi_1, \phi_2, \phi_3, \phi_4)^T \quad (4)$$

where $w_{ij}$ are weighting factors to define each color component in display. The calculated RGB components can be used to represent a "color" imaging of the object that include all the spectral phase information. As an example, if a weighting matrix $$W = \begin{bmatrix} 0.8 & 0 & 0 & 0 \\ 0 & 1.0 & 0 & 0 \\ 0 & 0 & 0.6 & 0 \end{bmatrix}$$

is used, the resulting image is shown in FIG. 18, where the difference of colors can further enhance some contrast features of the object.

To emphasize the main idea of this invention, the keys to successful implementations of all the eight embodiments concern a more efficient utilization of x-ray energy and dose. A method to generate a quasi-monochromatic spectrum is proposed for the DPC-CBCT imaging chain, which corresponds to the first, the second, the fifth and the sixth preferred embodiments. In addition, a method to obtain the spectral information of an object using the DPC-CBCT system is proposed as well, which corresponds to the third, the fourth, the seventh and the eighth preferred embodiments.

While preferred embodiments and variations thereon have been disclosed above, those skilled in the art who have reviewed the present disclosure will readily appreciate that other embodiments can be realized within the scope of the invention. For example, numerical values are illustrative rather than limiting. Also, any suitable technique or materials for manufacturing the grating can be used. Furthermore, the utility of the present invention is not limited to breast imaging, but instead can be applied to any biological or non-biological imaging. Therefore, the present invention should be construed as limited only by the appended claims.

We claim:

1. A method for cone beam CT imaging of an object, the method comprising:
   (a) acquiring projection images of the object taken at different view angles by using an imaging process that uses a polychromatic x-ray source, an energy-resolving detector having a plurality of energy channels, and a grating system;
   (b) said acquiring comprising acquiring, for each of the plurality of energy channels of the detector, a respective plurality of the projection images taken at different view angles;
   (c) performing three-dimensional (3D) computed tomography reconstructions of the object for each of the plurality of energy channels to produce a respective plurality of 3D reconstruction images; and
   (d) processing the plurality of 3D reconstruction images for each of the plurality of energy channels to produce one or more images of the object, wherein step (d) comprises assigning different weights to the images acquired from different energy channels.

2. The method of claim 1, wherein the object is a human breast being imaged using a half-cone geometry in which x-ray radiation from the x-ray source radiates the breast only without penetrating chest cavity or other body parts of the patient.

3. The method of claim 1, wherein step (d) comprises assigning different colors to weighted averages of images acquired from different energy channels.

4. A method for cone beam CT imaging of an object, the method comprising:
   (a) acquiring projection images of the object taken at different view angles by using an imaging process that uses a polychromatic x-ray source, an energy-resolving detector having a plurality of energy channels, and a grating system;
   (b) said acquiring comprising acquiring, for each of the plurality of energy channels of the detector, a respective plurality of the projection images taken at different view angles;
   (c) performing three-dimensional (3D) computed tomography reconstructions of the object for each of the plurality of energy channels to produce a respective plurality of 3D reconstruction images; and
   (d) processing the plurality of 3D reconstruction images for each of the plurality of energy channels to produce one or more images of the object, wherein step (d) comprises assigning different colors to weighted averages of images acquired from different energy channels, and wherein the different colors are assigned to the energy channels through a two-dimensional matrix of color weighting coefficients.

5. The method of claim 1, wherein the image is a matrix of a 3D distribution of phase coefficients.

6. The method of claim 1, wherein the image is a matrix of a 3D distribution of attenuation coefficients.

7. A method for cone beam CT imaging of an object, the method comprising:
(a) acquiring projection images of the object taken at different view angles by using an imaging process that uses a polychromatic x-ray source, an energy-resolving detector having a plurality of energy channels, and a grating system;
(b) said acquiring comprising acquiring, for each of the plurality of energy channels of the detector, a respective plurality of the projection images taken at different view angles;
(c) performing three-dimensional (3D) computed tomography reconstructions of the object for each of the plurality of energy channels to produce a respective plurality of 3D reconstruction images; and
(d) processing the plurality of 3D reconstruction images for each of the plurality of energy channels to produce one or more images of the object, wherein step (d) comprises assigning different colors to weighted averages of images acquired from different energy channels; wherein the image is a matrix of a 3D distribution of a density of sub-micron structures.

8. The method of claim 1, wherein the grating system comprises a steppable mechanism to perform phase-stepping use a source grating, a phase grating and an analyzer grating.

9. The method of claim 8, wherein the steppable mechanism comprises a linear stage that carries the source grating, the phase grating or the analyzer grating.

10. The method of claim 8, wherein the steppable mechanism has a plurality of branches where each branch has a grating set of a phase grating and an analyzer grating with a displacement corresponding to a successive set of phase steps.

11. The method of claim 8, wherein the steppable mechanism has a plurality of branches where each branch has a source grating that can be aligned to an optical axis through the object, with a displacement corresponding to a successive set of phase steps.

12. The method of claim 8, wherein the steppable mechanism produces a plurality of phase steps within one period and an intensity image is acquired at each phase step.

13. The method of claim 12, wherein a differential phase contrast image is computed from a plurality of the intensity images.

14. The method of claim 12, wherein an attenuation image is computed from the plurality of intensity images.

15. The method of claim 12, wherein a dark-field image is computed from the plurality of intensity images.

16. The method of claim 1, wherein the grating system comprises phase and analyzer gratings that are misaligned to produce a moire pattern.

17. The method of claim 16, wherein a differential phase contrast image is computed from the moire pattern.

18. The method of claim 17, wherein an attenuation image is computed from the moire pattern.

19. The method of claim 18, wherein a dark-field image is computed from the moire pattern.

20. The method of claim 1, further comprising, before step (a):
(i) imaging the object with an imaging process different from the imaging process of step (a)-(d) to determine a region of interest in the object; and
(ii) positioning the object so that the region of interest is positioned for steps (a)-(d).

21. The method of claim 20, wherein the imaging process different from the imaging process of steps (a)-(d) is computed tomography.

22. The method of claim 21, wherein the computed tomography is cone-beam computed tomography.

23. The method of claim 1, wherein step (b) comprises moving the x-ray source, the grating system and the detector relative to the object to define a data acquisition geometry.

24. A method for cone beam CT imaging of an object, the method comprising:
(a) acquiring projection images of the object at different view angles by using an imaging process that uses an x-ray source, a detector, a grating system and an x-ray beam filter;
(b) said acquiring comprising producing, with the beam filter, a quasi-monochromatic x-ray spectrum for differential phase contrast imaging; and
(c) performing three-dimensional (3D) computed tomography reconstructions using said projection images to produce one or more reconstruction images of the object wherein the reconstructed image is a matrix of a 3D distribution of a density of sub-micron structures.

25. The method of claim 24, wherein the object is a human breast being imaged using a half-cone geometry in which x-ray radiation from the x-ray source radiates the breast only without penetrating chest cavity or other body p arts of the patient.

26. The method of claim 24, wherein the reconstructed image is a matrix of a 3D distribution of phase coefficients.

27. The method of claim 24, wherein the reconstructed image is a matrix of a 3D distribution of attenuation coefficients.

28. The method of claim 24, wherein the grating system comprises a steppable mechanism to perform phase-stepping of a source grating, a phase grating and an analyzer grating.

29. The method of claim 28, wherein the steppable mechanism comprises a linear stage that carries the source grating, the phase grating or the analyzer grating.

30. The method of claim 28, wherein the steppable mechanism has a plurality of branches where each branch has a grating set of a phase grating and an analyzer grating with a displacement corresponding to a successive set of phase steps.

31. The method of claim 28, wherein the steppable mechanism has a plurality of branches where each branch has a source grating that can be aligned to an optical axis through the object, with a displacement corresponding to a successive set of phase steps.

32. The method of claim 28, wherein the steppable mechanism produces a plurality of phase steps within one period and an intensity image is acquired at each step.

33. The method of claim 32, wherein a differential phase contrast image is computed from a plurality of the intensity images.

34. The method of claim 32, wherein an attenuation image is computed from the plurality of intensity images.

35. The method of claim 32, wherein a dark-field image is computed from the plurality of intensity images.

36. The method of claim 32, wherein the grating system comprises phase and analyzer gratings that are misaligned to produce a moire pattern.

37. The method of claim 36, wherein the differential phase contrast images are computed from the moire pattern.

38. The method of claim 36, wherein an attenuation image is computed from the moire pattern.

39. The method of claim 36, wherein a dark-field image is computed from the moire pattern.

40. The method of claim 24, further comprising, before step (a):

(i) imaging the object with an imaging process different from the imaging process of steps (a) and (c) to determine a region of interest in the object; and
(ii) positioning the object so that the region of interest is positioned for steps (a) and (c).

41. The method of claim 40, wherein the imaging process different from the imaging process of steps (a) and (c) is computed tomography.

42. The method of claim 41, wherein the computed tomography is cone-beam computed tomography.

43. The method of claim 24, wherein step (a) comprises moving the x-ray source, the gratings and the detector relative to the object to define a data acquisition geometry.

44. The method of claim 24, wherein compared to a polychromatic spectrum, the quasi-monochromatic spectrum can reduce x-ray exposure to obtain the same image quality.

\* \* \* \* \*